United States Patent [19]

Tien et al.

[11] Patent Number: 5,687,722
[45] Date of Patent: Nov. 18, 1997

[54] SYSTEM AND METHOD FOR THE ALGEBRAIC DERIVATION OF PHYSIOLOGICAL SIGNALS

[75] Inventors: Jonathan Tien, Redmond; David R. Marble, Seattle, both of Wash.

[73] Assignee: SpaceLabs Medical, Inc., Redmond, Wash.

[21] Appl. No.: 507,754

[22] Filed: Jul. 26, 1995

Related U.S. Application Data

[63] Continuation-in-part of Ser. No. 442,834, May 17, 1995.

[51] Int. Cl.$^6$ .................................................. A61B 5/000
[52] U.S. Cl. .................................................. 128/633; 128/41
[58] Field of Search ........................... 128/633, 664–7; 356/39–41

[56] References Cited

U.S. PATENT DOCUMENTS

| | | | |
|---|---|---|---|
| 4,537,200 | 8/1985 | Widrow | 128/696 |
| 4,649,505 | 3/1987 | Zinser, Jr. et al. | 379/411 |
| 4,799,493 | 1/1989 | DuFault | 128/705 |
| 4,955,379 | 9/1990 | Hall | 128/633 |
| 4,956,867 | 9/1990 | Zurek et al. | 381/94.1 |
| 5,278,777 | 1/1994 | Cummins | 364/574 |
| 5,285,782 | 2/1994 | Prosser | 128/633 |
| 5,351,685 | 10/1994 | Potratz | 128/633 |
| 5,490,505 | 2/1996 | Diab et al. | 128/633 |
| 5,499,627 | 3/1996 | Steuer et al. | 128/633 |
| 5,553,615 | 9/1996 | Carim et al. | 128/633 |

FOREIGN PATENT DOCUMENTS

| | | |
|---|---|---|
| 0 314 331 | 5/1989 | European Pat. Off. . |
| WO 92 15955 | 9/1992 | WIPO . |
| WO 94 22360 | 10/1994 | WIPO . |

Primary Examiner—Jennifer Bahr
Assistant Examiner—Bryan K. Yarnell
Attorney, Agent, or Firm—Seed and Berry LLP

[57] ABSTRACT

A technique for the algebraic derivation of a pulse oximetry signal uses the mathematical relations of detected light signals. First and second light sources transmit light through the patient's finger or reflects light off the blood vessels in the patient's finger. A light detector detects light from each of the light sources and generates a measured intensity signal. The measured intensity signal includes the true intensity of light transmitted from each of the light sources as well as noise introduced during the measurement process. A data sample from each of the light sources is digitized and subdivided into a plurality of data windows. The mathematical relationship is applied to each of the data windows to determine a ratio value indicative of oxygen saturation in the patient. The ratio values are statistically analyzed to determine the best estimate for the correct ratio value. This ratio value is subsequently processed to determine the oxygen saturation within the patient.

28 Claims, 13 Drawing Sheets

SYSTEM AND METHOD FOR THE ALGEBRAIC DERIVATION OF PHYSIOLOGICAL SIGNALS

CROSS-REFERENCE TO RELATED APPLICATION

The present application is a continuation-in-part of U.S. patent application Ser. No. 08/442,834, filed on May 17, 1995, patent pending.

TECHNICAL FIELD

The present invention relates generally to signal processing and, more particularly, to a system and method for processing physiological signals in the presence of noise to derive the physiological signals.

BACKGROUND OF THE INVENTION

The measurement of physiological signals is difficult because the underlying physiological processes generate very low level signals and interfering noise is inherent in the body and the interface between the body and sensors of the physiological processes. For example, the measurement of electrocardiogram (ECG) signals is based on the electrical activity generated by the electrical depolarization of the heart muscle. The signals are typically detected by surface electrodes mounted on the chest of the patient. The signals are initially weak at the signal source (i.e., the heart) and are even weaker at the surface of the chest. Furthermore, electrical interference from the activity of other muscles, noise caused by patient breathing, general movement, and the like cause additional interference with the ECG signal. External electrical interference, such as 60 Hertz (Hz) interference, also compounds the ECG measurement problem. Therefore, great care must be taken in the design and use of physiological processors to enhance the quality of the desired signal and reduce the effects of interfering signals.

Another common physiological measurement that is made difficult by the presence of interfering noise is the measure of oxygen saturation in the blood. This measurement is frequently performed with a pulse oximeter 1, illustrated in the functional block diagram of FIG. 1. A transmissive pulse oximetry sensor 2 is placed on a finger 4 of the patient. First and second light sources 6 and 8 are directed through the fleshy portion of the finger 4 and detected by one or more light detectors 10 on the opposite side of the finger. As is well known in the art, the light from light sources 6 and 8 are of different wavelengths that are differentially absorbed by oxygenated blood cells. The first light source 6 is typically designated as a Red light source having a wavelength in the red region of the spectrum. The second light source 8 is typically designated the IR source having a wavelength in the near infrared region of the spectrum.

The pulse oximeter 1 determines the oxygen saturation based on a ratio of the light detected from the Red light source 6 and the IR light source 8, respectively. A ratio calculator 12 determines the ratio of detected light and uses the value of the ratio as an address in a look-up table 14. The look-up table 14 contains data relating the ratio of detected light to the oxygen saturation in the blood. A typical oxygen saturation curve 18 is illustrated in FIG. 2 where the percentage of oxygen saturation is plotted against the ratio of detected light from the Red light source 6 and the IR light source 8 (see FIG. 1). Pulse oximeters may also use reflective pulse oximetry sensors (not shown) in which the light sources and light detectors are positioned adjacent each other, and the light from the light sources is reflected back to the detector(s) by oxygenated blood cells in the finger 4.

The measurement of blood oxygen saturation is important for physicians who are monitoring a patient during surgery and at other times. As with other physiological measurements, pulse oximetry measurement also is susceptible to interference from noise. As is known in the art, pulse oximetry is particularly susceptible to interference from stray light and from patient motion. Stray light detected by the light detector 10 can cause erroneous calculation of the ratio. Known techniques are employed to reduce the interference caused by stray light. The interference from patient motion is a much more difficult noise source and is the subject of intensive research.

Therefore, it can be appreciated that there is a significant need for a system and method for measurement of physiological signals that enhances the desired signal in the presence of interfering noise signals. This and other advantages provided by the present invention are described in the detailed description and accompanying figures.

SUMMARY OF THE INVENTION

The present invention is embodied in a system and method for the enhancement of physiological signals in the presence of noise. The system includes a plurality of light sources directed toward the subject, each of which produces light of a different wavelength. A light detector is positioned to detect a plurality of light signals after passage through or reflection from the subject and to generate signals indicative of the intensity of the plurality of detected light signals. Each of the detected light signals has a first portion arising from light transmitted from a corresponding one of the plurality of light sources and a second portion arising from a plurality of interference light sources. A window generator generates first and second data windows derived from the plurality of detected signals. A storage location within the system contains a mathematical relationship of the first and second portions of the plurality of detected signals and a first ratio of the first portion of a first of the plurality of detected signals to the first portion of a second of the plurality of detected signals. A calculator uses the mathematical relationship to generate first and second functions using the first and second data windows, respectively. The first and second functions provide a solution value indicative of the first ratio.

The solution value may be a point of intersection between the first and second functions. Alternatively, the solution value is a statistical measure of the first ratio based on the solution value.

In one embodiment, the first ratio is indicative of blood oxygen saturation in the subject. The system further includes a lookup table containing data relating the first ratio to the blood oxygen saturation level. The first data window is derived from a number of possible sources such as a derivative of the first of the plurality of detected channels. Alternatively, the first data window may be the alternating current (AC) component of the first of the plurality of detected signals.

In another embodiment, the system is capable of measuring carbon monoxide levels in the blood. In this embodiment, three light sources are directed toward the subject. The window generator generates first, second, and third data windows derived from the first, second, and third detected signals. The mathematical relationship also includes a ratio of the first portion of the first detected signal with the first portion of a third detected signal. The calculator uses the mathematical relationship to generate first and second functions whose solution value is indicative of a first ratio. The calculator also generates a third function and calculates a solution value of the second and third functions to determine a second ratio. The second ratio is related to blood carboxy hemoglobin saturation.

In yet another embodiment, the system generates a plurality of data windows, each providing a solution value indicative of the first ratio. A statistical analyzer analyzes the solution values and determines a final value for the first ratio based on the plurality of solution values.

In one embodiment, the plurality of data windows are generated from a group of signals comprising the first detected signal, a mathematical derivative of the first detected signal, the second detected signal, a mathematical derivative of the second detected signal, a combination of the first and second detected signals, and a mathematical derivative of the combination of the first and second detected signals. Alternatively, the system may calculate an average value for each of the group of signals and place data whose value is less than the average for a particular one of the group of signals in a first data window and placing data whose value is greater than or equal to the average for the particular one of the group of signals in the second data window. Alternatively, the second data window may be derived by placing data whose value is greater than or equal to the average for a second one of the group of signals in the second data window.

DETAILED DESCRIPTION OF THE INVENTION

Figure 1:
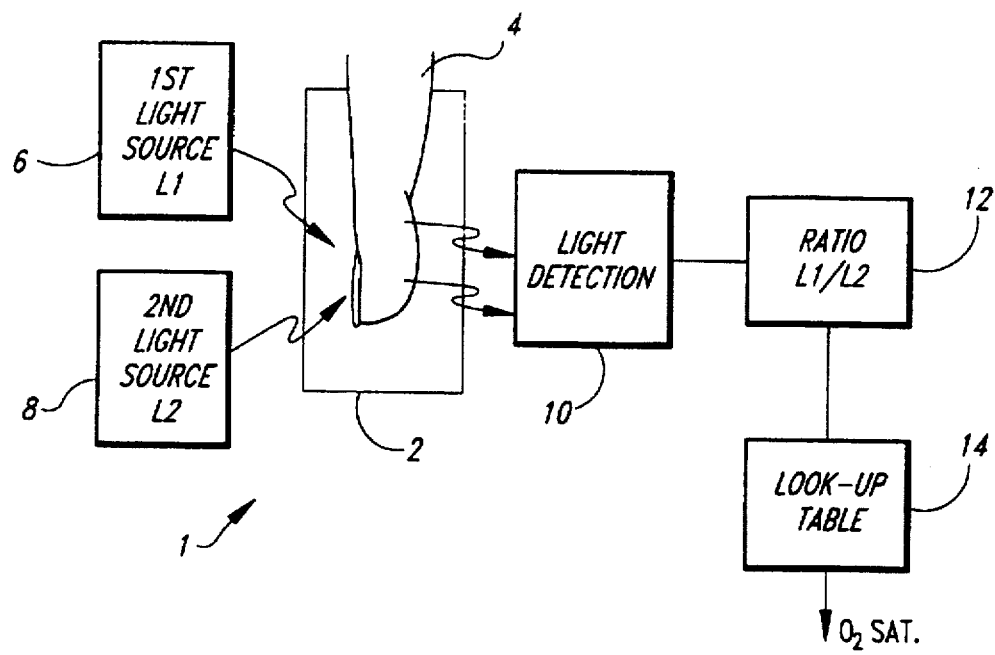
FIG. 1 is a functional block diagram of a prior art oximetry system.

Measurement of physiological signals in the presence of interference is a difficult task, particularly if the interference is somewhat random rather than periodic. A number of different techniques can potentially be used to separate the desired physiological signal from the interfering noise signal. For example, a filter can sometimes be used to remove the interfering noise signal. Notch filters, such as a 60 Hz notch filter, can be used to minimize interference from line noise. Similarly, high frequency interference noise signals can be eliminated with a lowpass filter designed to pass the physiological signal of interest and to reject frequencies above the physiological signal bandwidth. However, some interference sources have the same or similar frequency content as the physiological signal of interest. For interference of this type, different signal processing technologies must be employed.

Adaptive signal processing is one well known technique for the separation of a desired signal from an interference signal. Adaptive signal processing is based on the assumption that the noise caused by the interference signal is uncorrelated to the desired signal. A conventional adaptive signal processor, configured as a correlation canceller, is illustrated in the functional block diagram of FIG. 3. An adaptive processor 20 has a signal input 22 and a noise reference input 24. The noise reference input 24 is fed to an adaptive filter 28. The adaptive filter 28 generates a filter output 30 that is subtracted from the signal input 22 in a conventional subtractor 34. The subtractor 34 generates an error signal 38 having a value designated herein as $\epsilon$ that is fed back to the adaptive filter 28. The adaptive filter 28 is automatically adjusted so that the error signal 38 has a minimum correlation with the noise reference input 24. Thus, the adaptive filter 28 is adjusted so that the subtractor 34 cancels any correlated signal in the signal input 22. The error signal 38 is the system output and contains the portion of the input signal 22 that is uncorrelated to the noise reference input 24. In a typical application of adaptive filtering, the signal input 22 consists of a combination of a pure input signal from a device, such as a sensor, and a noise signal from one or more sources. The noise reference input 24 should then be a signal that is related to and at least partially correlated with, the noise signal. The adaptive filter 28 is adjusted so that the error signal 38 is the pure input signal since the pure input signal has a minimum correlation with the noise reference signal applied to the noise reference input 24.

Adaptive signal processing has been successfully applied to the measurement of physiological signals when the source of the interference signal is well characterized. For example, the physician may wish to listen to a fetal heartbeat whose acoustical signal strength is relatively small compared to the acoustical strength of the mother's heartbeat. As discussed above, simple filtering will not work satisfactorily because the two heartbeats have similar frequency content. However, adaptive signal processing can isolate the fetal heartbeat by using the much louder material heartbeat as the noise reference input 24 and the combination of fetal and maternal heartbeats as the signal input 22. Because the two heartbeats are uncorrelated and the maternal heartbeat can be independently derived, the adaptive signal processor 20 can easily isolate the fetal heartbeat. Similarly, the adaptive signal processor 20 can remove 60 Hz interference by simply using the 60 Hz signal as the noise reference input 24. Thus, adaptive signal processing can effectively remove the undesirable interference signal provided that the interference signal can be independently derived.

However, some physiological signals of interest do not have an independent interference source to use as the noise reference input 24. For example, pulse oximetry is susceptible to motion artifact, as described above. The motion alters the path that the light takes through the finger 4 (see FIG. 1) and the characteristics of the interface between the finger 4 and the sensor 2. As the light from the Red light source 6 and the IR light source 8 pass through the fleshy portion of the finger 4, each is contaminated by a noise signal, primarily due to patient motion. The detected light is thus the combination of the true light transmitted through the finger 4 plus the interfering noise introduced in the measurement process. This may be illustrated by the following equations:

$$R = R^* + N \quad (1)$$

$$r = r^* + n \quad (2)$$

where R is the light intensity measured by the light detector 10 (see FIG. 1), $R^*$ is the true intensity of light transmitted by the Red light source 6, and N is the noise source introduced by the measurement process while measuring the intensity of the Red light. Similarly, r in equation (2) is the light intensity measured by the light detector 10, $r^*$ is the true intensity of light transmitted by the IR light source 8, and n is the noise source introduced by the measurement process while measuring the intensity of the IR light.

The goal of the measurement process is to determine the ratio of the true intensity of Red light, $R^*$ transmitted through the finger 4 to true intensity of IR light, $r^*$ transmitted through the finger. However, most pulse oximetry system determine the ratio of the measured signal (i.e., R/r) or some processed version of the measured intensities due to an inability to determine the true intensity. The ratio of intensities, whether it is the ratio of measured intensities, true intensities, or some processed version of the measured intensities, is designated herein as $r_a$.

Some prior art pulse oximetry systems attempt to minimize the effects of motion artifact through conventional filtering or modulation of the intensity of the light sources 6 and 8. However, these processing techniques are not particularly effective because the motion artifact is caused primarily by movement of venous blood in the tissues of the finger 4 rather than from some external noise source such as stray light. Conventional filtering may remove some undesirable noise, but the frequency content of the motion artifact is similar to that of the desired signal. Modulation techniques may reduce interference from stray ambient light, but have little effect on motion artifact because the primary noise source (e.g., venous blood movement resulting from patient motion) originates in the measurement pathway. Thus, the ratio determined by many pulse oximetry systems is not accurate.

It should be noted that the intensity of detected light varies with the patient's heart beat thus creating a time-varying pulsatile waveform. The pulsatile waveform contains an alternating current (AC) signal component and a direct current (DC) component. A more accurate determination of the ratio $r_a$ is given by the following equation:

$$r_a = \frac{(Red_{AC}/Red_{DC})}{(IR_{AC}/IR_{DC})} \quad (3)$$

where $Red_{AC}$ is the AC component of the intensity of the measured Red light, R, $Red_{DC}$ is the DC component of the intensity of the measured Red light, $IR_{AC}$ is the AC component of the intensity of the measured IR light, r, and $IR_{DC}$ is the DC component of the intensity of the measured IR light. In practice, the DC components tend to cancel each other out thus normalizing the resultant ratio of AC components. Thus, equations (1) and (2) above may be more accurately shown as:

$$R(t) = R^*(t) + N(t) \quad (4)$$

$$r(t) = r^*(t) + n(t) \quad (5)$$

where $R(t) = Red_{AC}$ and $r(t) = IR_{AC}$ to reflect the time varying nature of the signals.

Figure 4:
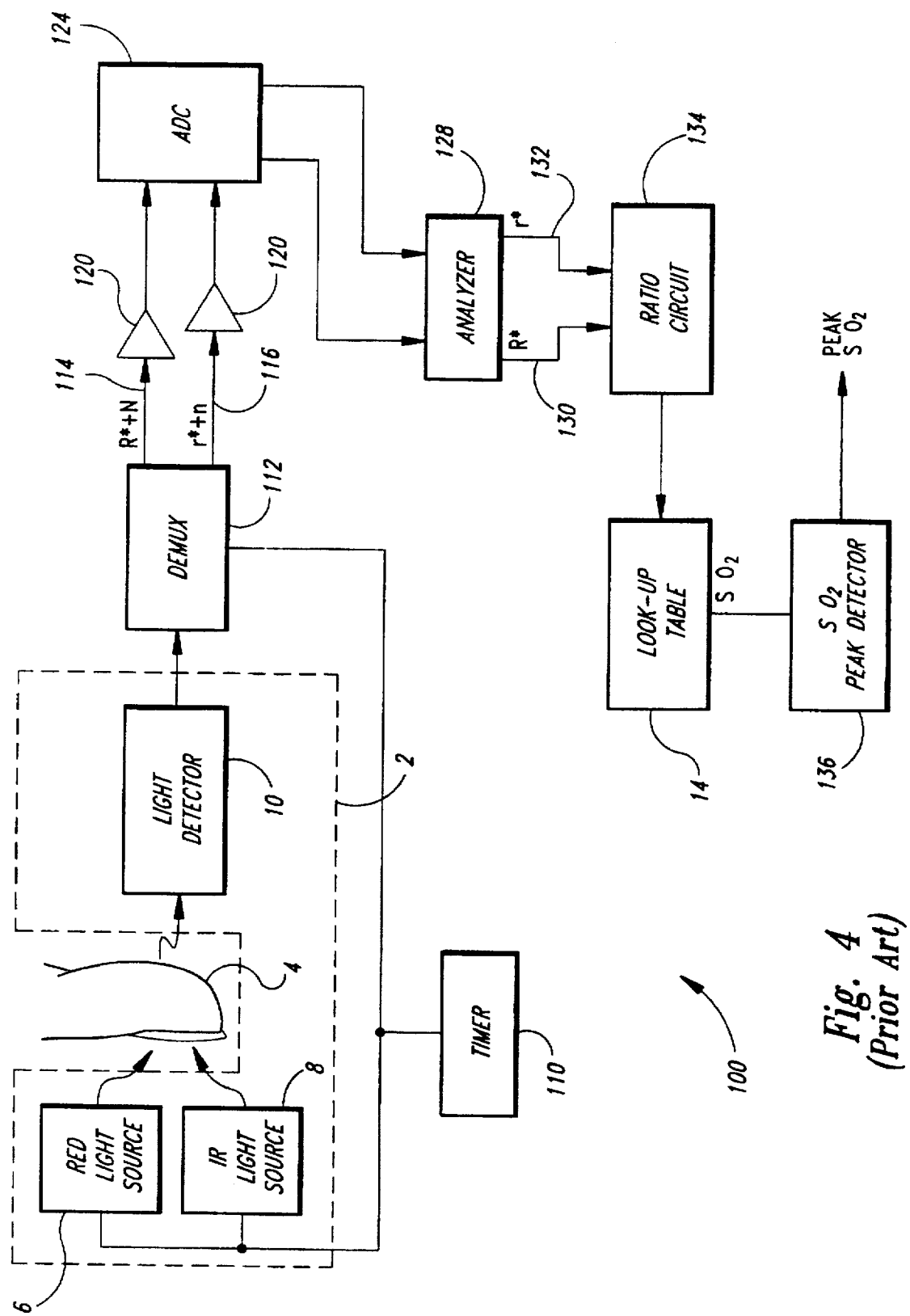
FIG. 4 is a detailed functional block diagram of the system of FIG. 1.
Figure 5:
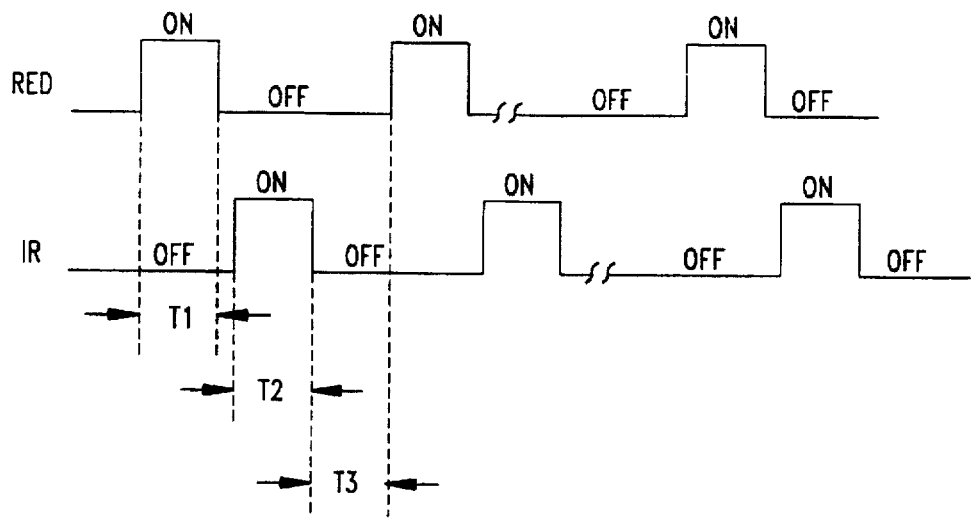
FIG. 5 are waveforms that illustrate the timing control of light sources used by the system of FIG. 4.

A typical prior an transmissive pulse oximetry system 100 is illustrated in the functional block diagram of FIG. 4, where the sensor 2 contains the Red light source 6 and the IR light source 8, typically on the same side of the patient's finger 4. The Red and IR light sources 6 and 8 are alternately activated by a timer 110. The activation timing of the first and second light sources 6 and 8 is illustrated in the waveform of FIG. 5. The Red light source 6 is activated in the period T1. Following the period T1, the IR light source 8 is activated during the period T2. Following the period T2, neither the Red light source 6 or the IR light source 8 is activated during the period T3. The pulse oximeter uses the period T3 to detect stray ambient light and determine a baseline value to compensate for the stray ambient light. Compensation of stray light is well known by those of ordinary skill in the an and will not be discussed herein. The timer 110 repeats the pulsation of the Red light source 6 and the IR light source 8 in the manner described above. It should be noted that the intensity of the light from the Red light source 6 and the IR light source 8 is automatically adjusted by a closed-loop system to assure an acceptable detected signal level. This closed-loop gain control is well known in the art and need not be discussed herein.

The detector 10 detects light transmitted through the fleshy portion of the finger 4. The signals generated by the light detector 10 are passed to a demultiplexor 112. The demultiplexor 112 is coupled to the timer 110 and is controlled by the timer 110 to generate an independent signal for the light detected from each of the light sources 6 and 8, respectively. The time division multiplexing used by the system 100 is well understood and will not be discussed in detail herein. As discussed above, the timer 110 enables the Red light source 6 during the period T1. During that same period T1, the timer also controls the demultiplexor 112 so that the detected signals from the Red light source 6 are routed to a data line 114. During the time period T2, the timer 110 enables the IR light source 8 and controls the demultiplexor 112 so that the detected signals from the IR light source are routed to a data line 116. Each of the data lines 114 and 116 can be coupled to optional amplifiers 120. The amplified signals are coupled to the inputs of an analog to digital converter (ADC) 124 that digitizes the signal in a conventional manner. It should be noted that the amplifiers 120 may be integrally formed as part of the ADC 124. The ADC 124 may also include optional lowpass filters (not shown) to assure that the analog signals are bandlimited below the Nyquist rate of the ADC.

The demultiplexor 112 is shown as a separate component in FIG. 4 for the sake of clarity. Those skilled in the art will recognize that the demultiplexing function can also occur after the signal from the light detector 10 has been digitized. The present invention is intended to encompass all such conventional techniques for demultiplexing the signals from the light detector 10.

The ratio circuit 12 receives the digitized signals and uses the ratio of R(t)/r(t) to determine a location in the look-up table 14. Assuming that no motion artifact is present, the data entry in the look-up table 14 corresponds to the blood oxygen saturation. In reality, the ratio calculated by the ratio circuit 12 may be inaccurate because of the motion artifact.

Figure 3:
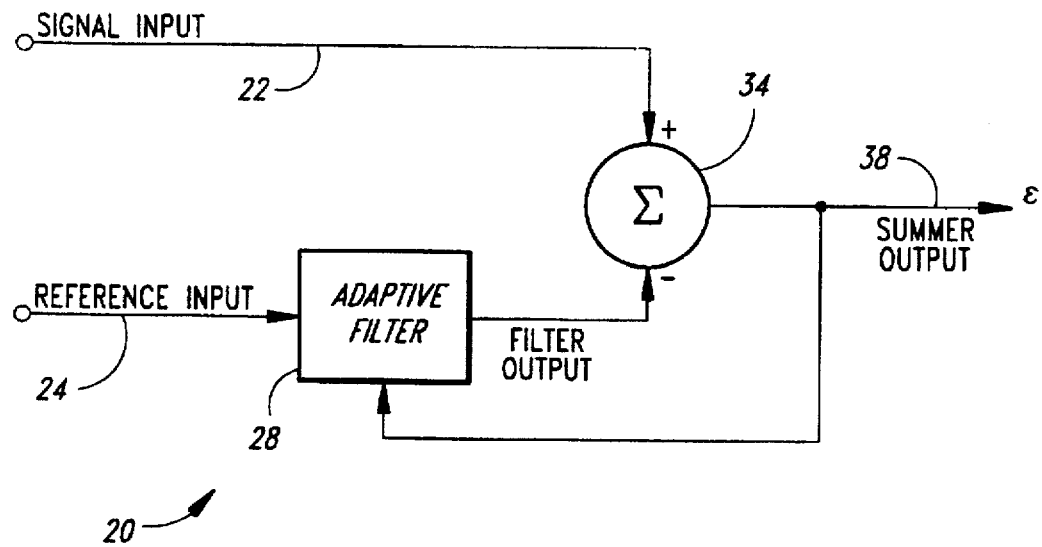
FIG. 3 is a functional block diagram of a conventional adaptive signal processor.

A technique has been developed to use the conventional adaptive signal processor of FIG. 3 to eliminate the motion artifact. A reference signal related to the motion artifact interference source is independently derived and applied as the noise reference input 24 to the adaptive signal processor 20 (FIG. 3). The noise reference input 24 uses detected signals from the Red and IR light sources 6 and 8. These techniques are described in PCT Patent Publication No. WO92115955, published on Sep. 17, 1992. The system described in this publication generates a noise reference signal related to the interference noise and uses this noise reference in the correlation canceller version of the adaptive signal processor 20 shown in FIG. 3. The adaptive signal processor 20 uses the noise reference to cancel the noise in the measured signal thus resulting in a signal that is representative of the true signal (i.e., the measured signal minus the noise signal).

The noise reference signal generated by the prior art pulse oximeter has the following form:

$$N(t)=R(t)-\omega r(t) \quad (6)$$

where N(t) is the time varying noise reference signal, R(t) is the time varying detected signal from the Red light source 6 (i.e., true intensity plus noise), r(t) is the time varying signal from the detected signal from the IR light source 8 (i.e., true intensity plus noise) and $\omega$ is a selected value of the ratio $r_a$. Equation (6) has been empirically derived to model the noise source.

Figure 2:
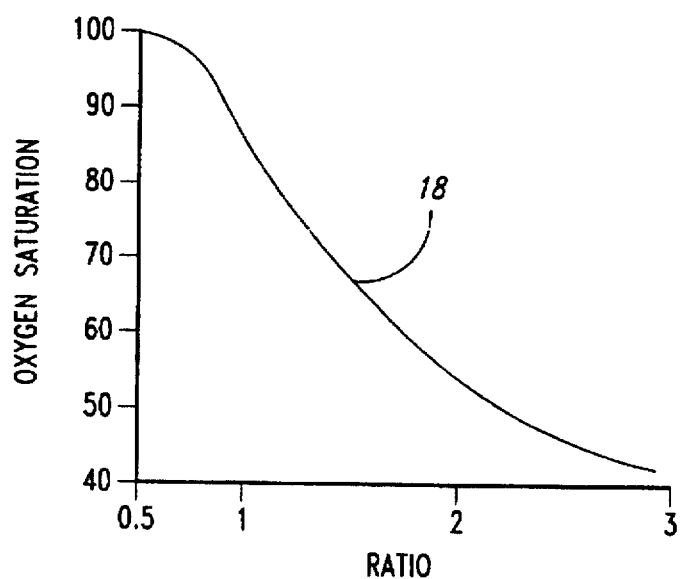
FIG. 2 is a typical oxygen saturation curve employed by the system of FIG. 1 to determine blood oxygen saturation.

As can be seen from Equation (6) above, the prior art pulse oximeter must determine a value for $\omega$ in order to generate the noise reference signal N(t). As seen in FIG. 2, the ratio of the light intensities and thus the value of $\omega$ lies within a range from 0.5 to 3.0. The limitation in the range of values for $\omega$ is imposed by the physiology. That is, the oxygen saturation value lies between 100% and 0%, with the corresponding ratios lying between a value of 0.5 to 3.0, respectively. To compensate for variations in the sensitivity of the sensor 2, a range of ratio values from 0.3 to 3.0 is typically used. The prior art pulse oximeter takes advantage of the knowledge that the ratio must lie within the range from 0.3 to 3.0 and scans the entire range of possible values for the ratio and inserts each of these values into equation (6) above. The noise reference signal for each possible value of the ratio $r_a$ is provided as the noise reference input 24 (see FIG. 3) to the adaptive signal processor 20. The adaptive signal processor 20 in turn generates the value $\epsilon$ for each of the possible values of the ratio. A typical output of the value $\epsilon$ versus the ratio $r_a$ is illustrated by a waveform 48, shown in FIG. 6. The best estimate of the value of $\omega$ is given by a peak 50 or a peak 52 of the waveform 48. It is known that if the value of $\omega$ corresponds to the peak 50, then N(t) in equation (6) equals $C_1 n(t)$ where $C_1$ is a constant and n(t) is the noise source introduced by the measurement process while measuring the intensity of light from the IR source 8 (see FIG. 5). If the value of $\omega$ corresponds to the peak 52, it is known that N(t) in equation (6) equals $C_2 r^*(t)$ where $C_2$ is a constant and r*(t) is the true intensity of light transmitted by the IR light source 8. The value of $\omega$ corresponding to the peak 50 is inserted into equation (6) above to generate a noise reference signal N(t) as the noise reference input 24 (see FIG. 3) of the adaptive signal processor 20. The error signal 38 is the noise signal n(t) if the value of $\omega$ corresponds to the peak 52. However, by selecting the value of $\omega$ corresponding to the peak 50, the reference signal N(t) corresponds to the noise signal n(t). In this case, the correlation canceller adaptive signal processor 20 cancels out the constant $C_1$ as well as correlated signals between the signal input 22 and the noise reference input 24 such that the error signal 38 is the desired signal r*(t). The true output signals are provided to the ratio circuit 12 (see FIG. 4) and processed in the manner previously described.

The disadvantage of this prior art approach is that generating the value $\epsilon$ for each of the possible values of the ratio $r_a$ is a computationally difficult and time consuming approach to adaptive filtering in pulse oximetry. As those skilled in the art can appreciate, real-time calculation of blood oxygen saturation is important to the physician. This real-time constraint can only be met with the prior art approach using expensive and powerful digital signal processor (DSP) hardware.

Figure 7:
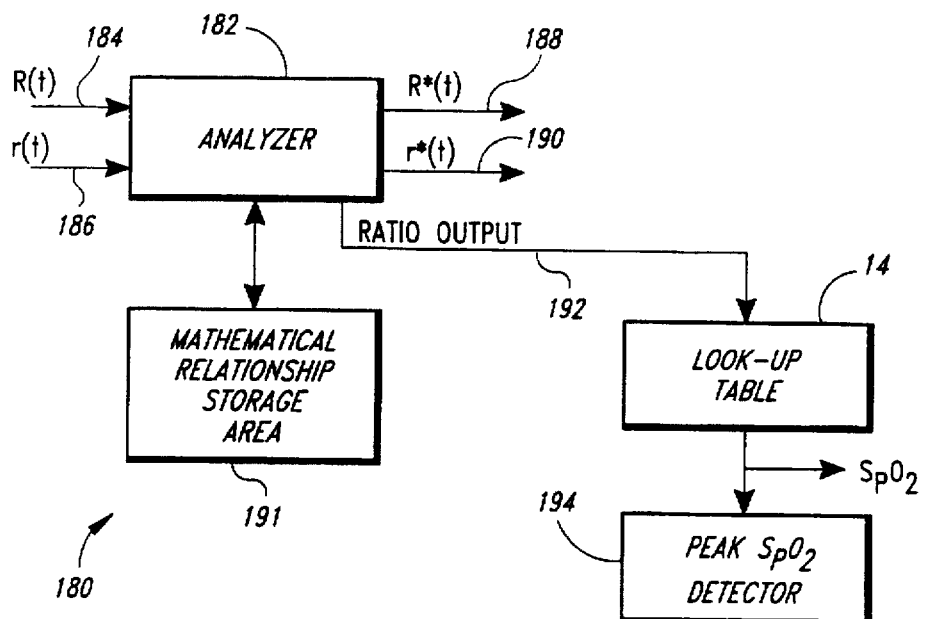
FIG. 7 is a functional block diagram of the present invention used with the system of FIG. 4.

An alternative approach to the measurement of blood oxygen saturation is described in U.S. patent application Ser. No. 08/442,834 and embodied in a system 180, shown in the functional block diagram of FIG. 7. This approach provides a more efficient computational process that does not generate the noise reference required by the prior art approach. Rather, the desired signal (i.e., the true intensity) is directly generated and does not use correlation cancellation techniques in the adaptive signal processor. An analyzer 182 coupled to the ADC 124 (see FIG. 4) receives digitized signals 184 representing the measured light intensity, R(t), from the Red light source 6, and digitized signals 186 representing the measured light intensity, r(t), from the IR light source 8. The analyzer 182 processes these signals using mathematical relationships between the measured signals and the true intensities, to generate a true intensity output 188 equal to the true intensity, R*(t), and a true intensity output 190 equal to the true intensity, r*(t). The mathematical relationships are stored in a mathematical relationship storage area 190 for use by the analyzer 182.

The analyzer 182 generates the ratio $r_a$ of true intensities (i.e., R*(t)/r*(t)) in the process of generating the true intensity outputs 188 and 190. A ratio output 192 is coupled to the lookup table 14 to permit the determination of oxygen saturation in a conventional manner. The output of the lookup table 14 is a value $S_pO_2$ corresponding to the blood oxygen saturation. The system 180 may also include an optional $S_pO_2$ peak detector 194 to generate signals indicative of the peak oxygen saturation. The true intensity outputs 188 and 190 are useful for monitoring the patient oximetry waveforms and for calculating continuous blood pressure measurements. Techniques for calculating blood pressure from pulse oximetry output waveforms are described in U.S. Pat. No. 5,269,310. The advantage of the present invention is that the signal that is directly generated is the desired signal rather than the noise reference signal. Furthermore, the processing techniques of the present invention require far fewer computational steps, thus improving the rate at which accurate data can be obtained.

Figure 6:
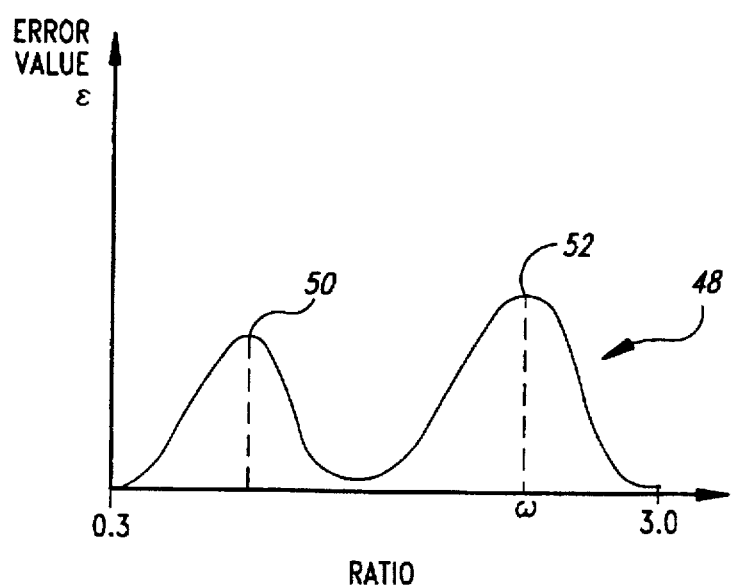
FIG. 6 illustrates a waveform used in the calculation of a reference noise signal by the conventional adaptive signal processor of FIG. 3.

With respect to FIG. 6, research has shown that the peak 50 corresponds to the ratio of the true intensities (i.e., R*(t)/r*(t)), while the peak 52 corresponds to the ratio of noise intensities (i.e., N(t)/n(t)). The following description provides details of the mathematical derivation of the reference signals representing the true intensities. For purposes of the following description, the ratio of the true intensities may be defined by the following equation:

$$\alpha = \frac{R^*(t)}{r^*(t)} \quad (7)$$

where $\alpha$ is the value of the ratio $r_a$ corresponding to the peak 50 (see FIG. 6), $R^*(t)$ is the time varying true intensity of light transmitted from the Red light source 6 and $r^*(t)$ is the time varying true intensity of light transmitted from the IR light source 8. The ratio of noise signals introduced by the measurement process is defined by the equation:

$$\beta = \frac{N(t)}{n(t)} \quad (8)$$

where $\beta$ is the value of the ratio $r_a$ corresponding to the peak 52 (see FIG. 6), $N(t)$ is the noise introduced during the measurement of the light transmitted by the Red light source 6 and $n(t)$ is the noise introduced during the measurement of the light transmitted by the IR light source 8. It is also known that the following constraint exists between $\alpha$ and $\beta$:

$$0.3 < \alpha < \beta < 3.0 \quad (9)$$

because of the physiological nature of the signals. It is noted that the percentage of oxygen saturation is also a time-varying signal, changing by approximately 0.5% over time. However, it is assumed that the blood oxygen saturation is constant over the short period required to perform the measurements. Thus, $\alpha$ and $\beta$ can be considered ratio constants for purposes of the present discussion.

Given equations (4)–(5) and (7)–(8), it is possible to express the relationship between $\alpha$ and $\beta$ using the following matrix equation:

$$\begin{bmatrix} 1 & 0 & 1 & 0 \\ 0 & 1 & 0 & 1 \\ 1 & -\alpha & 0 & 0 \\ 0 & 0 & 1 & -\beta \end{bmatrix} \times \begin{bmatrix} R^*(t) \\ r^*(t) \\ N(t) \\ n(t) \end{bmatrix} = \begin{bmatrix} R(t) \\ r(t) \\ 0 \\ 0 \end{bmatrix} \quad (10)$$

where it is assumed that $\alpha \neq \beta$. As previously stated, it is known that the primary cause of noise in transmissive pulse oximetry measurements is motion artifact caused by the movement of venous blood in the finger 4. Thus, the value $\beta$ in equation (8) is related to oxygen saturation in the venous blood. The assumption that $\alpha \neq \beta$ is based on the understanding that $\alpha$ is a measure of arterial blood oxygenation while $\beta$ is related to venous blood oxygenation. As the body takes oxygen from the blood, blood oxygenation decreases as blood moves from the arterial portion of the circulation system to the venous portion of the circulation system. Thus, the measure of arterial oxygenation, measured by $\alpha$, is not the same as $\beta$, which is related to venous oxygenation.

The significance of equation (10) is that all signal components can be explicitly calculated as a function of the input signals and the ratio constants $\alpha$ and $\beta$. The true signal components, $R^*(t)$ and $r^*(t)$ can also be explicitly derived using equation (10) above. The true signal components, $R^*(t)$ and $r^*(t)$, can be expressed in terms of the measured signals, $R(t)$ and $r(t)$, by the following equations, which are derived from equation (10):

$$R^*(t) = \frac{\alpha R(t) - \alpha \beta r(t)}{\alpha - \beta} \quad (11)$$

$$r^*(t) = \frac{R(t) - \beta r(t)}{\alpha - \beta} \quad (12)$$

Similarly, the noise signals, $N(t)$ and $n(t)$, can be expressed in terms of the measured signals, $R(t)$ and $r(t)$, by the following equations, which are also derived from equation (10):

$$N(t) = \frac{\alpha \beta r(t) - \beta R(t)}{\alpha - \beta} \quad (13)$$

$$n(t) = \frac{\alpha r(t) - R(t)}{\alpha - \beta} \quad (14)$$

It will be noted that the above equations (11)–(14) provide the true signal components, $R^*(t)$ and $r^*(t)$, and the noise components, $N(t)$ and $n(t)$, as a function of the measured signals, $R(t)$ and $r(t)$, available from the sensor 2 (see FIG. 4) and the ratio constants $\alpha$ and $\beta$. The values of the ratio constants $\alpha$ and $\beta$ are not known and must be determined by the system 180.

The measurement system described in PCT Patent Publication Number WO92115955, published on Sep. 17, 1992, requires a determination of a peak value for the ratio $r_a$. This system steps through each and every possible value of the ratio $r_a$ over the physiological range for the ratio $r_a$ to determine the peak value. Only then can the peak value be substituted into equation (6) to generate the noise reference signal. This is a tedious and time consuming process to determine the blood oxygen saturation. The correlation cancellation techniques described above with respect to PCT Patent Publication Number WO92115955 require a powerful and expensive digital signal processor to determine the blood oxygen saturation in real-time.

Various embodiments of the analyzer 182 are described in U.S. patent application Ser. No. 08/442,834. The analyzer 182 does not require a noise reference signal generated by the measured signals as does the prior art oximeter. Rather, the analyzer 182 directly derives a true intensity output 188 corresponding to the true intensity $R^*$ of light transmitted through the finger 4 from the Red light source 6 (see FIG. 4) and a true intensity output 132 corresponding to the true intensity $r^*$ of light transmitted through the finger from the IR light source 8. The system 180 uses the ratio of $R^*(t)/r^*(t)$ (i.e., $\alpha$) and the oxygen saturation curve 18 (see FIG. 2) to determine the blood oxygen saturation in a conventional manner.

Figure 8:
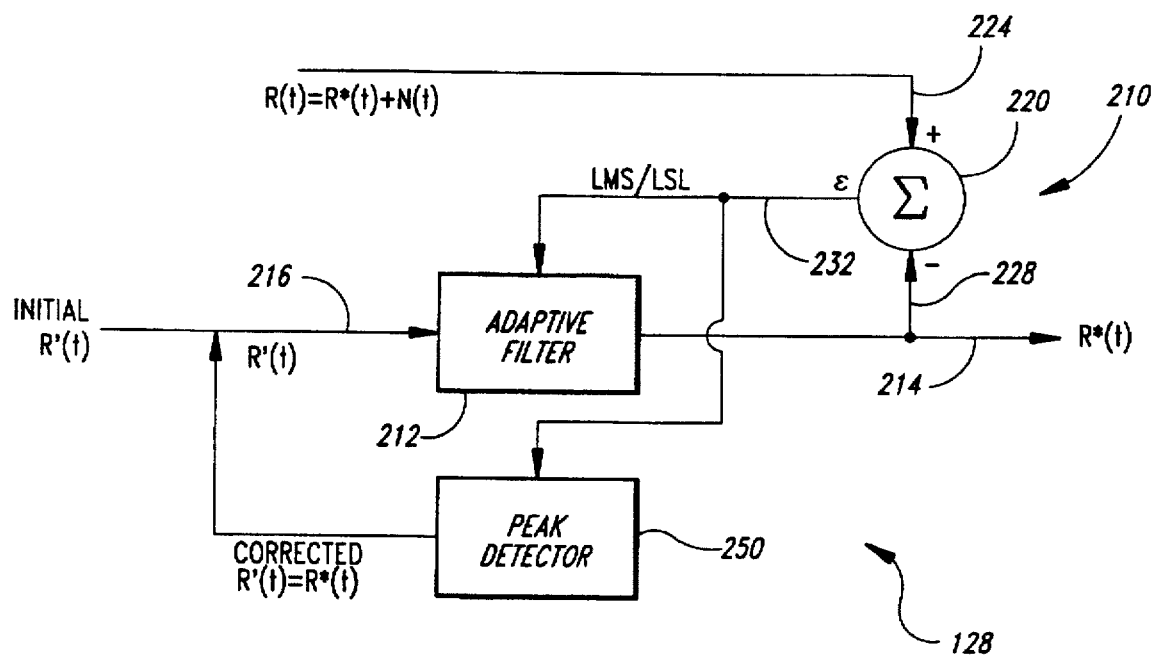
FIG. 8 illustrates a first embodiment of the system of FIG. 7.

A first embodiment of the analyzer 182, shown in the functional block diagram of FIG. 8, uses an adaptive signal processor 210. Although similar to the adaptive signal processor 20 of FIG. 3, the adaptive signal processor 210 does not use correlation cancellation techniques with a noise reference signal. Rather, the adaptive signal processor has an adaptive filter 212 with a filter output 214 that directly generates the desired output signal $R^*(t)$ if the appropriate signal is selected for a reference input 216 to the adaptive filter.

A subtractor 220 has a positive subtractor input 224 and a negative subtractor input 228. The measured signal $R(t)$, which is the combination of the true signal, $R^*(t)$, and the noise signal, $N(t)$, is coupled to the positive subtractor input 224, while the filter output 214 is coupled to a negative subtractor input 228. The subtractor 220 generates an error signal 232 that is fed back to the adaptive filter 212 in a well known manner. The adaptive signal processor 210 uses an iterative process to adjust the adaptive filter 212 to minimize the error signal 232. Minimization techniques, such as least mean squares (LMS) or least squares lattice (LSL), are used to adjust the adaptive filter 212. These techniques are well known in the art of adaptive signal processing and need not be discussed herein.

The reference input 216 is provided with a signal $R'(t)$ derived from equation (11) to estimate the true intensity $R^*(t)$. The signal $R'(t)$ is simply the signal of equation (11)

for selected values of the ratio $r_a$ over the range from 0.3 to 3.0 to determine values for the ratio $r_a$ corresponding to the peaks 50 and 52, respectively. The analyzer 182 does not scan the entire range from 0.3 to 3.0 as does the prior art pulse oximeter. In contrast, only selected values for the ratio $r_a$ between 0.3 and 3.0 are used to determine the correct values of the ratio constants α and β thus resulting in a more computationally efficient approach to pulse oximetry. Furthermore, the prior art reference signal of equation (6) must be used as a reference signal in the correlation cancellation adaptive signal processor 20 of FIG. 3, so that the error signal 38 is the desired signal. In contrast, the analyzer 182 of the present invention directly generates the desired signals using the mathematical relations of equation 10. When the correct values for the ratio constants α and β have been determined, the function $R'(t)=R^*(t)$. Again, it should be noted that the signal generated by the analyzer 182 is mathematically derived and equals the desired true intensity if the correct values are selected for α and β. This approach is markedly different from the prior art approach to adaptive signal processing because no noise reference signal is generated and no noise canceller is used by the adaptive signal processor 210. The true signal is determined directly from the given conditions and the mathematically derived relationships shown in the equations above. The adaptive filter 212 can be designed in a well known manner to improve the accuracy and correctness of the true signal. The procedure for the selection of the proper values for the ratio constants α and β is discussed below.

It should be noted that the above discussion relates to the measurement of the true intensity of light transmitted from the Red light source 6. However, those skilled in the art can readily recognize that the same principles apply to the measurement of the true intensity of light transmitted from the IR light source 8. The true intensity signal $r^*(t)$ can be directly derived from the true intensity signal $R^*(t)$ using the relationship of equation (7). Thus, both true intensity signals $R^*(t)$ and $r^*(t)$ can be directly derived once the correct values have been determined for the ratio constants α and β.

As stated above, the signal $R'(t)$ provided to the reference input 216 is equation (11) for selected values of the ratio $r_a$. The system 180 determines values for α and β so that $R'(t)=R^*(t)$, to assure that the filter output 214 will represent the true signal intensity $R^*(t)$. As previously illustrated by equation (9) above, the value of the ratio constants α and β lie between 0.3 and 3.0. The system 180 uses a peak detector 250 to derive the values of the ratio constants α and β without scanning the entire range. The peak detector 250 detects a peak in the error signal 232 over the physiological range of values for the ratio $r_a$. The physiological range for the ratio $r_a$ is divided in half and the peak detector 250 determines whether a peak lies in the first half of the subdivided range or the second half. If the peak detector 250 detects a peak in the first half of the subdivided range for the ratio $r_a$, it discards the second half. Conversely, if the peak is detected in the second half of the physiological range, the first half is discarded. The peak detector 250 repeats this process (i.e., divide and peak detect) until a peak is detected with sufficient accuracy. This approach provides a great computational advantage over the prior art since far fewer calculations are performed to detect the peak value.

The analyzer 182 (see FIG. 7) produces the ratio output 192, and the value for oxygen saturation $S_pO_2$ may be determined in a conventional manner. The optional peak detector 194 may be used to determine peak $S_pO_2$ levels. Thus, the analyzer 812 (see FIG. 7) directly produces reference signals equal to the true intensities. In practice, these true intensity signals are derived from the filter output 214. This direct calculation of the true intensities is performed without having to generate a noise reference signal as is done in the prior art, and without having to use digital signal processing correlation cancellation techniques that require a significant number of computational steps. Furthermore, the analyzer 182 requires significantly fewer calculations to determine accurate values for the ratio constants α and β.

Other embodiments of the analyzer 182 are also illustrated in U.S. patent application Ser. No. 08/442,834. However, these embodiments need not be described herein. The pulse oximetry system described in U.S. patent application Ser. No. 08/442,834 is computationally efficient because it rapidly determines the peak value for the ratio $r_a$ without having to scan the entire physiological range of values as do systems of the prior art. However, this process still requires a powerful computational device such as a digital signal processor to generate the adaptive filter. Those skilled in the art will readily recognize that the cost of a typical digital signal processor can make a product undesirably expensive.

The techniques described in the present invention generate the desired results without having to determine the peak values for the ratio $r_a$ and, furthermore, without requiring an expensive digital signal processor. Indeed, the principles of the present invention can be implemented on a conventional digital computer.

Figure 9:
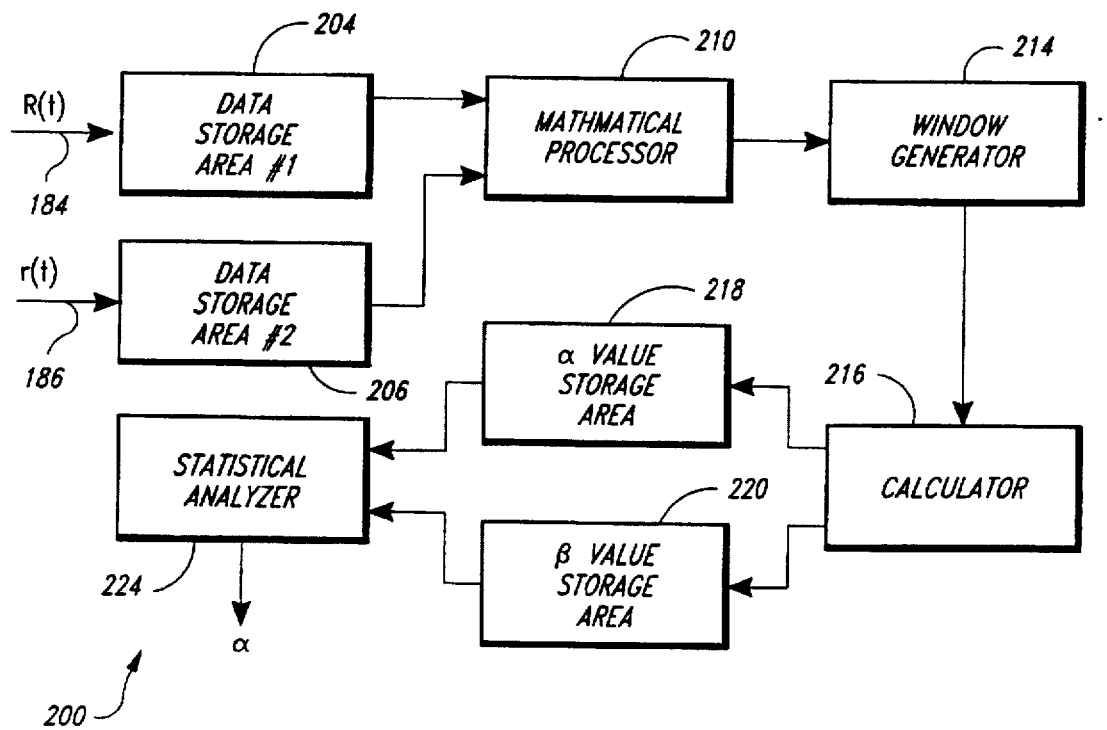
FIG. 9 is a function block diagram of the window generation and analysis system of the present invention.

The present invention is embodied in a system 300, shown in the functional block diagram of FIG. 9. The digitized signals 184 (see FIG. 7) representing the measured light intensity $R(t)$, from the Red light source 6, are stored in a first data storage area 204. The digitized signals 186 representing the measured light intensity, $r(t)$, from the IR light source 8 are stored in a second data storage area 206. The first and second data storage areas 204 and 206 store the digitized signals 184 and 186, respectively, for a predetermined measurement period. The predetermined period is selected such that the oxygen saturation value can be considered a constant. In one embodiment, the first and second data storage areas 204 and 206 store approximately five seconds of the digitized signals 184 and 186, respectively.

A mathematical processor 210 receives the digitized signals from the first and second data storage areas 204 and 206. The mathematical processor 210 calculates AC values and derivatives of the digitized signals 184 and 186. As will be described in detail below, the mathematical processor 210 may also calculate squared values of digitized signals 184 and 186 and calculates averages of the squared signals, the AC signals, and the derivatives. A window generator 214 separates the digitized data into a plurality of pairs of windows based on the characteristics of the data and certain measurement criteria. The characteristics of the data in the measurement criteria used by the window generator 214 will be described in detail below.

A calculator 216 calculates a plurality of (α, β) pairs for each of the plurality of pairs of windows determined by the window generator 214. Thus, the output of the calculator 216 is a set of α and β pairs. The alpha values are stored in an α value storage area 218, and the β values are stored in β value storage area 220. A statistical analyzer 224 receives the α and β value data from the α value storage area 218 and the β value storage area 220, respectively. The statistical analyzer 224 performs statistical analysis on the α and β value data to determine the most likely value for α. The output of the statistical analyzer 224 is the correct value α for the digitized signals 184 and 186. The oxygen saturation and peak oxygen saturation may be determined using the lookup table 14 (see FIG. 4) and the peak detector 136 in a conventional manner. The analysis steps performed by the mathematical processor 210, the window generator 214, the calculator 216, and the statistical analyzer 224 do not require the sophisticated and powerful data processing capabilities of a digital signal processor. Therefore, the system 200 may be implemented on a conventional digital computer and is capable of producing real time results at a significantly lower cost than systems employing digital signal processor technology.

It can be shown that the ratio constants $\alpha$ and $\beta$ are interrelated. If one assumes that the true signal and the noise signal are uncorrelated, the signals r*(t) and n(t) are said to be "orthogonal." This may be defined mathematically by the following equation:

$$\int_t r^*(t)n(t) = 0 \qquad (15)$$

which may also be expressed as:

$$\int_t \frac{(\alpha r(t) - R(t))(R(t) - \beta r(t))}{(\alpha - \beta)^2} = 0 \qquad (16)$$

by conventional mathematical manipulation of equations (10)–(15).

Using the previous assumption that $\alpha \neq \beta$, the following equations relate the ratio constants $\alpha$ and $\beta$:

$$\alpha = \frac{\int_t R^2(t) - \beta \int_t R(t)r(t)}{\int_t R(t)r(t) - \beta \int_t r^2(t)} \qquad (17)$$

$$\beta = \frac{\int_t R^2(t) - \alpha \int_t R(t)r(t)}{\int_t R(t)r(t) - \alpha \int_t r^2(t)} \qquad (18)$$

which solve equation (16) for $\alpha$ and $\beta$, respectively.

As seen in equations (17) and (18), the ratio constants $\alpha$ and $\beta$ are symmetric and thus only one independent variable, either $\alpha$ or $\beta$, need be determined. The following description provides an example of the determination of the values of the ratio constants $\alpha$ and $\beta$.

As discussed above, the ratio constant $\beta$ is related to oxygen saturation in the venous system. While a curve similar to that of FIG. 2 has not been developed to indicate the oxygen saturation for the venous system, it is known that the ratio constant $\beta$ can provide some measure of oxygen saturation in the venous system. For purposes of the present invention, it is assumed that oxygen consumption in the tissue is constant over the short duration of the measurement process.

There are an infinite number of $(\alpha, \beta)$ pairs that provide valid solutions to equations (17) and (18). The equations are illustrated graphically in FIG. 10A where the digitized data 184 and 186 provide a set of valid $(\alpha, \beta)$ pairs. An $\alpha$ curve 260 provides a graphical representation of all valid values for $\alpha$ and $\beta$ that solve equation (17). Similarly, a $\beta$ curve 264 provides a graphical representation of all valid values for $\alpha$ and $\beta$ that solve equation (18). The symmetry of the $\alpha$ curve 260 and the $\beta$ curve 264 graphically illustrate the symmetry between $\alpha$ and $\beta$ previously discussed with respect to equations (17) and (18).

If the same equations (17) and (18) are solved for a second data window, the result would be a second set of valid $(\alpha, \beta)$ pairs. The second data window is generated by the window generator 214 (see FIG. 9) from the same digitized signals 184 and 186 used to generate the first data window. The calculator 214 generates the second set of valid $(\alpha, \beta)$ pairs, which are graphically illustrated in FIG. 10B. The techniques used to generate the data windows will be discussed in detail below.

A second $\alpha$ curve 260' provides a graphical representation of all valid values for $\alpha$ and $\beta$ that solve equation (17) for the second data window. Similarly, a second $\beta$ curve 264' provides a graphical representation of all valid values for $\alpha$ and $\beta$ that solve equation (18) for the second data window. As discussed above, the system 200 assumes that the oxygen saturation remains constant over the short time required to collect the data for analysis. Thus, the data from the first data window and the data from the second data window should result in the same values for $\alpha$ and $\beta$. In this ideal setting, there is only one correct value for $\alpha$ and one correct value for $\beta$. The correct values are indicated by the intersection of the curves shown in FIG. 10B. Specifically, an intersection 262 is the intersection of the first and second $\alpha$ curves 260 and 260' and is the only value for $\alpha$ and $\beta$ that satisfies equation (17) for both the first and second data windows. Similarly, an intersection 266 is the intersection of the first and second $\beta$ curves 264 and 264' and is the only value for $\alpha$ and $\beta$ that satisfies equation (18) for both the first and second data windows. The symmetry of equations (17) and (18) is also illustrated by the intersections 262 and 266, which have identical coordinates, with the ordinate and abscissa values interchanged.

Figure 10A:
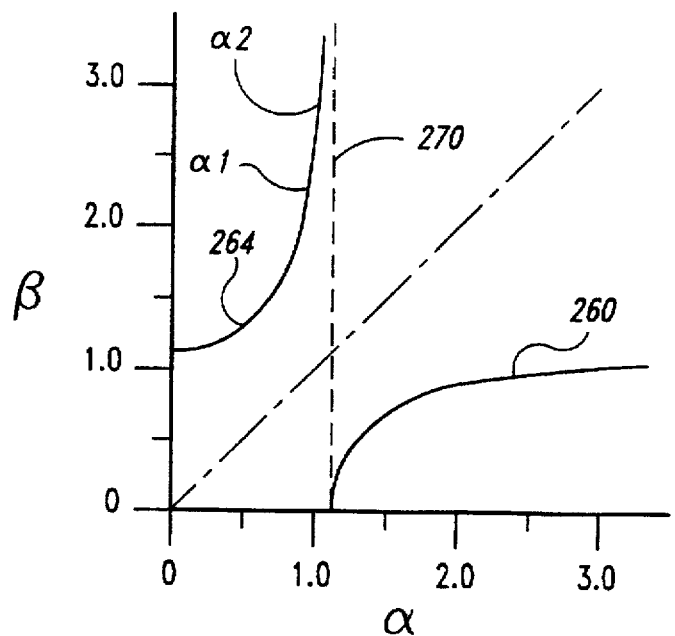
FIG. 10A is a graphical illustration of the equation used by the system of FIG. 9 for a first data window.
Figure 10B:
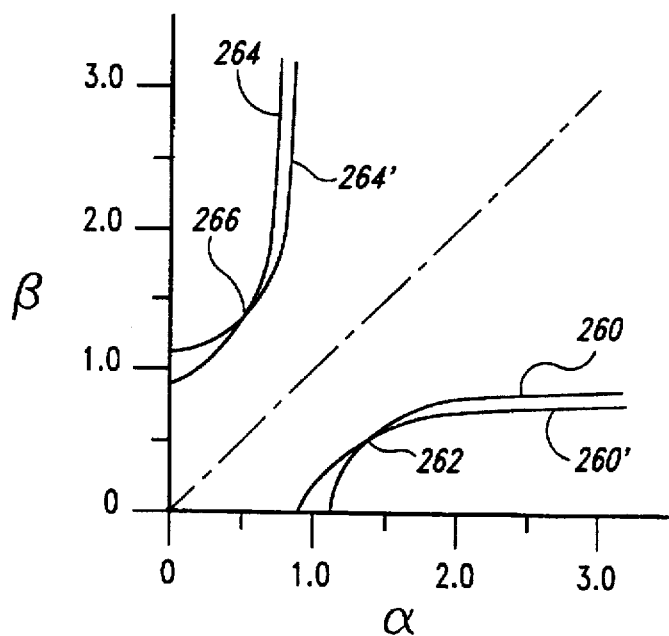
FIG. 10B is a graphical illustration of the equation used by the system of FIG. 9 for first and second data windows.

While measurement technique used by the system 200 is illustrated graphically in FIG. 10B, the system uses an analytical approach to solving for the correct values of $\alpha$ and $\beta$. Equation (17) may be rewritten in the form illustrated below:

$$\alpha_1 = F_1(\beta)$$

$$\alpha_2 = F_2(\beta) \qquad (19)$$

so as to express $\alpha$ as a function of $\beta$ for the first and second data windows, respectively. The specific form of equation (17) is rewritten as follows:

$$\alpha_i = Fi(\beta) = \frac{\int_t R_i^2(t) - \beta \cdot \int_t R_i(t) \cdot r_i(t)}{\int_t R_i(t) \cdot r_i(t) - \beta \cdot \int_t r_i^2(t)} \qquad (20)$$

where i=1 to 2 for the two data windows, respectively. Since, for a short period of time $\alpha$ and $\beta$ are constant, $\alpha_1 = \alpha_2$. Thus, it is possible to set $F_1(\beta) = F_2(\beta)$ and solve for $\alpha$ and $\beta$. The solution yields a pair of quadratic equations having the following form:

$$(\alpha,\beta) = \left\{ \begin{array}{l} \int_t r_1^2(t) \int_t R_2^2(t) - \int_t R_1^2(t) \int_t r_2^2(t) \\[8pt] \mp \left[ \begin{array}{l} \left( \int_t r_1^2(t) \int_t R_2^2(t) - \int_t r_1^2(t) \int_t R_2^2(t) \right)^2 - \\[6pt] 4 \times \left( \int_t r_1^2(t) \int_t R_2(t)r_2(t) - \int_t R_1(t)r_1(t) \int_t r_2^2(t) \right) \times \\[6pt] \left( \int_t R_1(t)r_1(t) \int_t R_2^2(t) - \int_t R_1^2(t) \int_t R_2(t)r_2(t) \right) \end{array} \right]^{1/2} \end{array} \right\} \times$$

$$\left[ 2 \times \left( \int_t r_1^2(t) \int_t R_2(t)r_2(t) - \int_t R_1(t)r_1(t) \int_1 r_2^2(t) \right) \right]^{-1} \quad (21)$$

This process results in a pair of values for $(\alpha,\beta)$ so long as different data windows are used for $F_1(\beta)$ and $F_2(\beta)$.

Figure 11A:
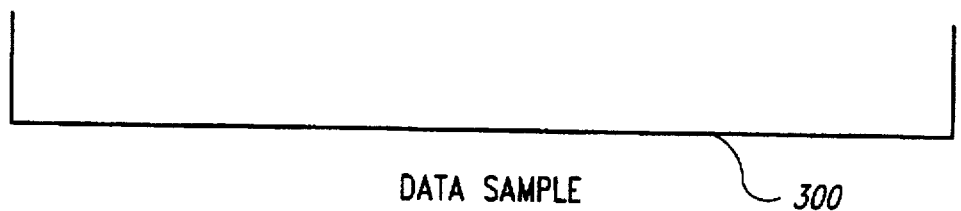
FIGS. 11A–11C illustrate the use of multiple data windows by the system of FIG. 9.
Figure 11B:
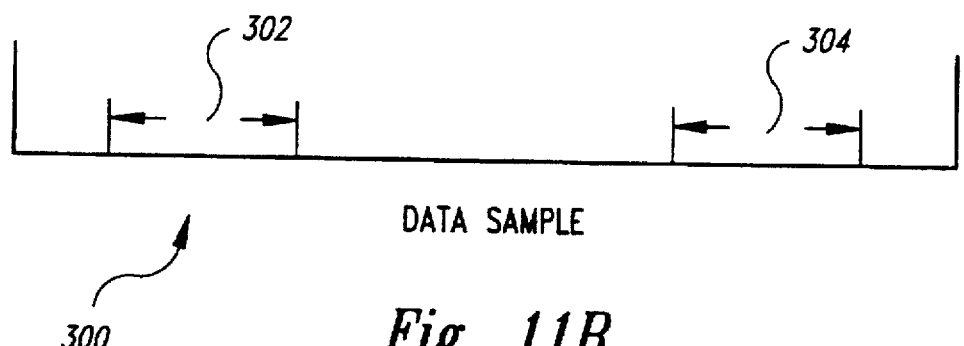
Figure 11C:
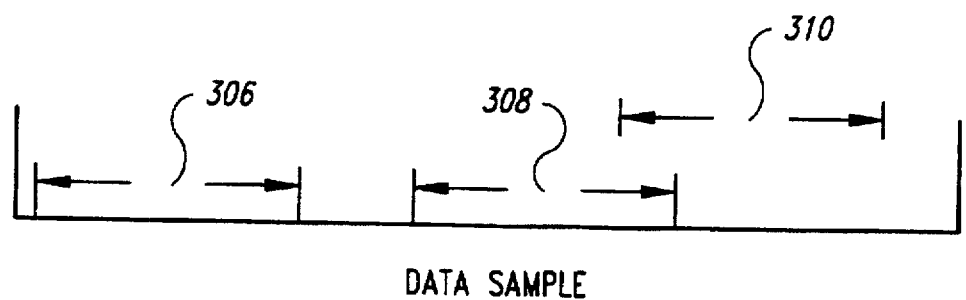

The selection of data windows by the window generator 214 (see FIG. 9) is illustrated in FIGS. 11A–11C. In FIG. 11A, a data sample 300 is provided to the system 200 for each of the digitized signals 184 and 186. As previously noted, the precise length of the data sample 300 is not critical. However, the data sample 300 must be sufficiently short in length to validate the assumption that oxygen saturation is constant. In one embodiment, the data sample 300 may be five seconds in length. However, the principles of the present invention are not limited by the precise length of the data sample 300. In FIG. 11B, a first data window 302 and a second data window 304 are derived from the data sample 300. In the case of the two data windows 302 and 304, the system 200 will provide two $(\alpha, \beta)$ pairs. As illustrated in FIG. 10B, the correct $\alpha$ and $\beta$ values may be ascertained by the intersections 262, and 266, respectively. As illustrated in FIG. 11C, first, second, and third data windows 306, 308, and 310 result in three $(\alpha, \beta)$ pairs. The first $(\alpha, \beta)$ pair results from solving equation (21) using the first and second data windows 306 and 308. The second $(\alpha, \beta)$ pair results from solving equation (21) for the second and third data windows 308 and 310 while the third $(\alpha, \beta)$ pair results from solving equation (21) for the first and third data windows 306 and 310. Thus, any combination of two data windows from the data sample 300 will provide an $(\alpha, \beta)$ pair. It should be noted that the data windows will frequently overlap in time, such as illustrated in FIG. 11C. The data windows may be generated in a variety of different manners. For example, the data window 308 may be the derivative of the data sample 300, while the data window 310 may be the AC component of the data sample.

The window generator 214 (see FIG. 9) may generate data windows in a number of different manners. In one embodiment, only two data windows are generated. For example, the data windows may be different time segments of the data sample, such as illustrated by the first and second data windows 302 and 304 in FIG. 11B. Alternatively, the first data window 302 is generated using the AC component of the digitized signals 184 and 186 for the entire data sample 300, while the second data window 304 is generated by taking the derivative of the digitized signals for the entire data sample. It should be noted that whenever a data window is generated for the digitized signal 184, the corresponding data points from the digitized signal 186 form part of the same data window. For example, consider a data sample in which the digitized signals 184 and 186 are each 500 data points long. Whenever a data point from one of the digitized signals 184 and 186 are placed in the first data window, the corresponding data point from the other of the digitized signals is also placed in the same data window. In the example above, if data point n, where n=1 to 500 in the above example, of the digitized signal 184 is placed in the first data window, then data point n of the digitized signal 186 is also placed in the first data window. Conversely, if a particular data point, such as data point n+1 of the digitized signal 184 is placed in the second data window, then data point n+1 of the digitized signal 186 is also placed in the second window. Thus, whenever first and second data windows are generated by the window generator 214, it contains the corresponding data points from both digitized signals 184 and 186. In this manner, equation (20) uses corresponding data points from the digitized signals 184 and 186 in each of the respective data windows.

To determine the derivative of the digitized signals 184 and 186, the mathematical processor 210 (see FIG. 9) performs a point-to-point derivative in which the slope from data point n to data point n+1 is calculated for each of the data points in the first data storage area 204. A similar calculation is performed on the digitized signal 186 for the data points stored in the second data storage area 206. The AC component of the digitized signals 184 and 186 are determined by calculating an average value for all data points in the first data storage area 204. This average value is subtracted from each of the data points in the first data storage area. A similar calculation is performed on the digitized signal 186 and the data points stored in the second data storage are 206. This calculation effectively removes the DC component of the digitized signals 184 and 186.

Alternatively, the window generator 214 (see FIG. 9) generates data windows based on both statistical knowledge and clinical knowledge about the nature of the physiological signal. The mathematical process 210 (see FIG. 9) calculates six average values from the initial data sample 300. These six average values are the square of the AC component $(Red_{AC}^2)$ of the measured signal R(r) from the Red light source 6 (see FIG. 4), the square of the derivative of the measured signal from the Red light source $(dR(t)/dt^2)$, the square of the AC component $(IR_{AC}^2)$ of measured signal from the IR light source 8, the square of the derivative of the measured signal from the IR light source $(dr(t)/dt^2)$, the product of the AC components of each of the measured signals from the Red light source and the IR light source ($Red_{AC}*IR_{AC}$) and the derivative of the product of the measured signals (($dR(t)/dt)*(dr(t)/dt$)). As those skilled in the art will readily recognize, calculating the average value of the AC component itself would result in a value of zero. For this reason, the average values calculated by the mathematical processor 210 are typically squared values.

The window generator 214 selects data points for each data window based on the size of a particular data point compared to the average value for that particular parameter. For example, one pair of data windows may be derived based on the measured signal from the Red light source 6. In this example, all data points for which $Red_{AC}$ is less than or equal to the average AC component will be in a first window, while all data points for which the $Red_{AC}$ is greater than or equal to the average value will be in a second data window. Similar comparisons are performed for each of the remaining five averages described above. Thus, for each of the six averages calculated by the mathematical processor 210, the window generator 214 divides the data sample 300 into a pair of windows with data points that are less than or equal to the average for a particular parameter being placed in one data window for the parameter, while the data points that are above average for that parameter are placed into a second data window.

In addition to the six pairs of data windows derived from the six averages described above, the window generator 214 generates two additional data windows based on the relative size of the AC components of the measured signals ($Red_{AC}$ and $IR_{AC}$). If a particular data point for the $Red_{AC}$ signal is less than or equal to the corresponding data point for the $IR_{AC}$ signal, that data point is assigned to a first data window. If the particular data point of the $Red_{AC}$ signal is greater than or equal to the corresponding data point of the $IR_{AC}$ signal, that data point is placed in the second data window. Similarly, an additional pair of data windows is generated by the window generator 214 based on the relative sizes of the derivatives of the measured signals ($dR(t)/dt$ and $dr(t)/dt$). Thus, the window generator 214 can generate eight pairs of data windows from the data sample 300. The optimum window pairs would have all noise in one window and all signal in the corresponding window. However, the data points within a particular window are generally a mixture of both noise and signal. However, based on the characteristics of the data, and the placement of data in one window or another based on its value relative to an average value for a particular parameter, it can be expected that, for each pair of data windows, one data window will contain more signal, while the other corresponding data window will contain more noise.

As previously discussed, if a particular data point derived from the digitized signal 184 is placed in the first data window, the corresponding data point derived from the digitized signal 186 is also assigned to the first data window. In contrast, if the particular data point derived from the digitized signal 184 is placed in the second data window, the data point the window generator would 214 also assign the corresponding data point derived from the digitized signal 186 to the second data window regardless of its actual value. In this manner, a pair of data windows may be generated based on the average value of a particular signal derived from the digitized signal 184.

Alternatively, the window generator 214 may analyze the data points derived from the digital signal 186 and classify those data points as belonging in the first or second data window based on their value relative to the average value of the particular parameter derived from the digitized signal 186. If the window generator 214 performs this analysis on the data points derived from the digitized signal 186, the corresponding data points derived from the digitized signal 184 are assigned to the first or second data window based only on the analysis of the data points derived from the digitized signal 184 and not based on the value of the data points derived from the digitized signal.

The calculator 216 (see FIG. 9) may use any number of combinations of the windows generated by the window generator 214. For example, the calculator 216 may use the AC components, $R_{AC}$ and $r_{AC}$, and the derivative values $dR(t)/dt$, and $dr(t)/dt$, to generate six different window pairs, as shown in Table 1 below.

TABLE 1

| Combination | First Data Window | Second Data Window |
|---|---|---|
| 1. | $R_{AC}$ | $r_{ac}$ |
| 2. | $R_{AC}$ | $\frac{dR(t)}{dt}$ |
| 3. | $R_{AC}$ | $\frac{dr(t)}{dt}$ |
| 4. | $r_{AC}$ | $\frac{dR(t)}{dt}$ |
| 5. | $r_{AC}$ | $\frac{dr(t)}{dt}$ |
| 6. | $\frac{dR(t)}{dt}$ | $\frac{dr(t)}{dt}$ |

As those skilled in the art can appreciate, a large number of possible data window combinations can be generated by the window generator 214 using the average values discussed above. The present invention is not limited by the specific combination of data windows used by the calculator 216. As discussed above, the average value calculated by the mathematical processor is used by the window generator 214 as a threshold value. Any data points in the first data storage area that are less than or equal to the threshold value are placed in the first data window, while data points that exceed the threshold value are placed in the second data window. As discussed above, the corresponding data points in the second data storage area 206 are placed in the same data window as the corresponding data point in the first data storage area 204. By selecting an average value, and classifying data points based on this average value, it can be expected that for each pair of data windows, one data window will contain more noise while the other will contain more signal.

As discussed above, equation (21) results in a pair of valid ($\alpha, \beta$) pairs under predetermined conditions. It is not initially known which of the values corresponds to $\alpha$ and which value corresponds to $\beta$. However, the value for $\alpha$ can subsequently be determined imposing the following clinical condition:

$$0.38 R_{DC}/r_{DC} < \alpha < \beta < 3.0 * R_{DC}/r_{DC} \qquad (22)$$

It should be noted that equation (22) is identical to equation (9) above except for the introduction of the DC component ratio in equation (22). The DC components merely indicate that the values for $\alpha$ and $\beta$ have not been normalized in the manner discussed with respect to equations (3)–(5). As those skilled in the art can appreciate, normalization of the measured signals, R(t) and r(t), prior to analysis by the system 200 could result in the loss of useful data prior to calculating the average values discussed above.

The calculator 216 (see FIG. 9) solves equation (21) for $\alpha$ and $\beta$. The values of $\alpha$ and $\beta$ determined by the calculator 216 typically satisfy equation (22). However, in some circumstances, the values of α and β do not meet the requirements of Equation (22). For example, in certain circumstances, the digitized signals 184 and 186 may contain significant amounts of noise.

Figure 12A:
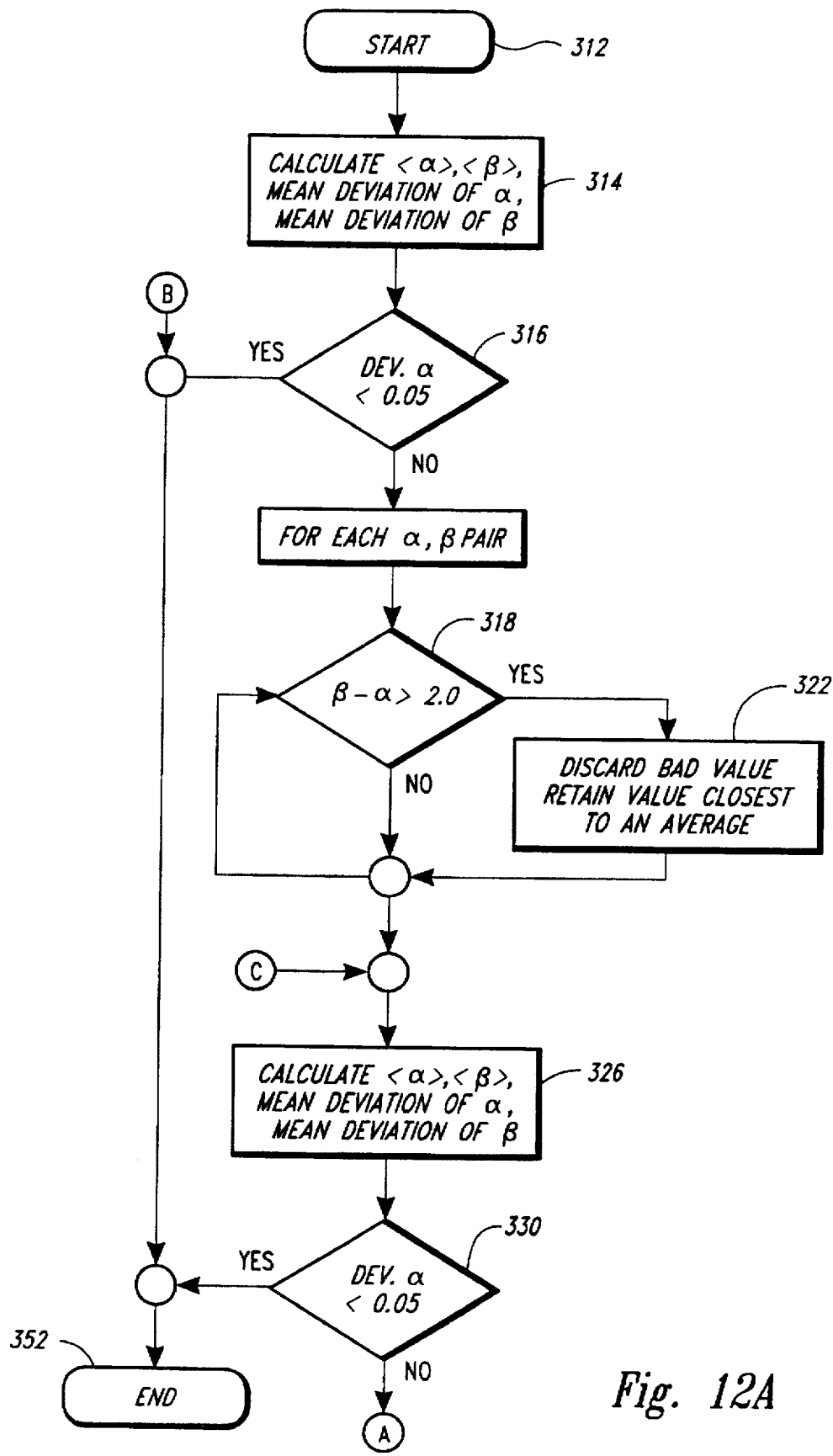
FIGS. 12A and 12B are flowcharts illustrating the statistical analysis performed by the system of FIG. 9.
Figure 12B:
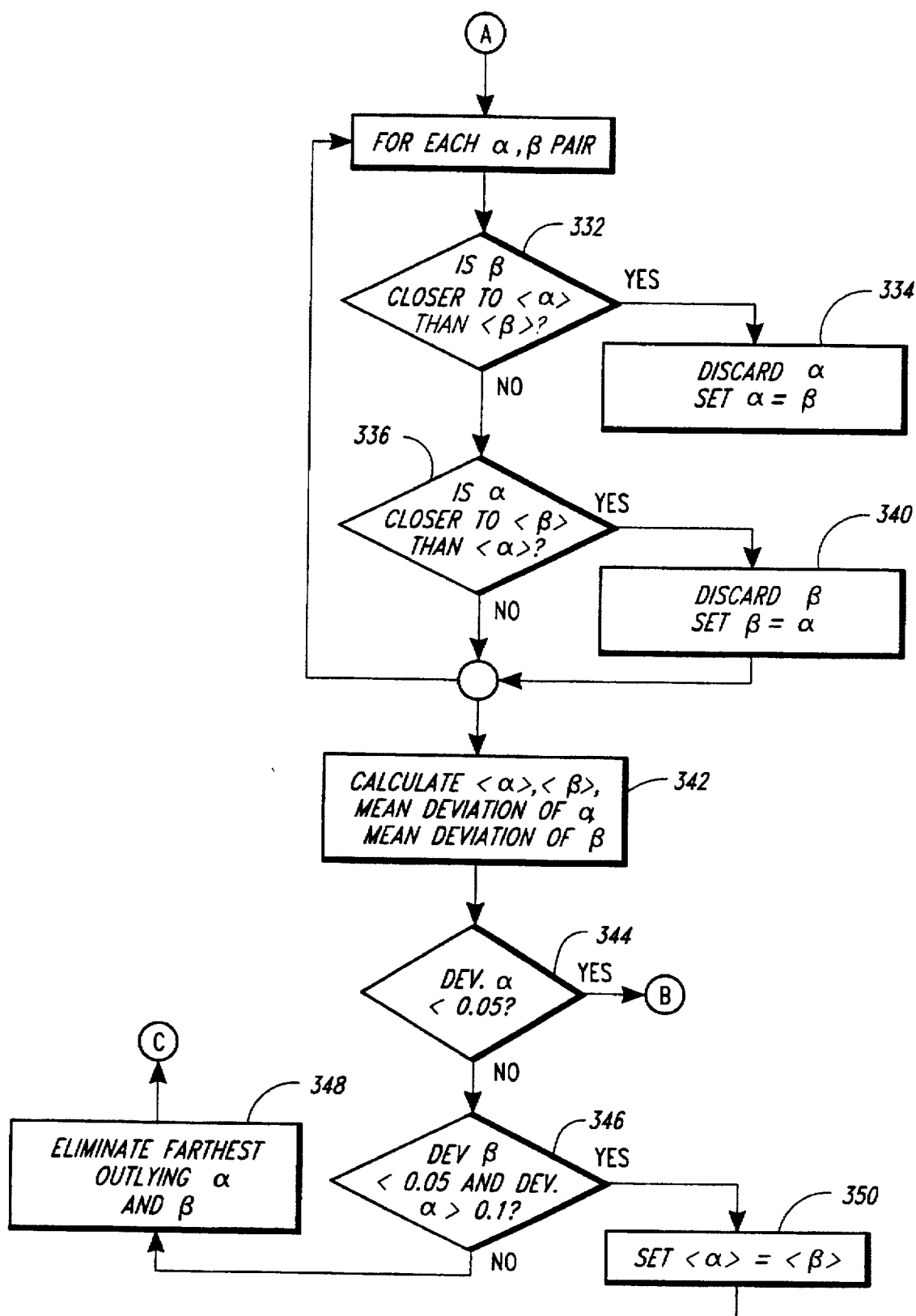

The statistical analyzer 224 (see FIG. 9) uses statistical techniques to determine an accurate value for α. The above example illustrated the operation of the system 200 using only two data windows generated by the window generator 214. In one embodiment, the system 200 calculates a new (α, β) pair approximately once per second. This new (α, β) pair is analyzed along with the previous 11 (α, β) pairs to drive a statistical measure of α. This process is illustrated in the flowchart of FIGS. 12A and 12B.

At the start 312, the system 200 has a new sample of the digitized data 184 and 186 (see FIG. 9). In step 314, the statistical analyzer 224 calculates the average values for α and β from 12 (α, β) pairs including the present (α, β) pair and the previous 11 (α, β) pairs. In addition, the statistical analyzer 224 calculates the mean deviation for the 12 (α, β) pairs. In decision 316, the statistical analyzer determines whether the deviation of α is less than 0.05. If the deviation of or is less than 0.05, the system accepts the new value for α and ends the process in step 352. If the deviation of α is not less than 0.05, the result of decision 316 is NO.

In that event, the statistical analyzer 224 performs a measurement on each of the 12 (α, β) pairs. For each of the 12 (α, β) pairs, the statistical analyzer tests, in decision 318, whether β-α is greater than 2.0. If β-α is greater than 2.0, the result of decision 318 is YES. In that event, one value of the particular (α, β) pair is considered invalid. In step 322, the statistical analyzer keeps the value that is closer to either the α or the β average. This process is repeated for each of the 12 (α, β) pairs.

Following the analysis of each of the 12 (α, β) pairs, the statistical analyzer 224 enters a loop in which data is processed until the deviation of α is less than a predetermined value. In step 326, the statistical analyzer 224 recalculates average values for α, β, mean deviation of α, and a mean deviation of β. In decision 330, the statistical analyzer 224 determines whether the deviation of α is less than 0.05. If the deviation of α is less than 0.05, the result of decision 330 is YES. In that case, the present value for α is accepted, and the system ends the process in step 352. If the deviation of α is not less than 0.05, the result of decision 330 is NO. In that event, the statistical analyzer 224 performs additional analysis for each of the 12 (α, β) pairs. In decision 332, the statistical analyzer 224 tests to determine whether the value for β is closer to the average value for α than it is to the average value for β. If the value for β is closer to the average α value than it is to the average β value, the result of decision 332 is YES. In that event, in step 334, the statistical analyzer 224 discards the value for α and sets α equal to the value for β. Following step 334, the statistical analyzer 224 moves to decision 336. If the β value is not closer to the average α value than it is to the average β value, the result of decision 332 is NO. In that event, the statistical analyzer moves to decision 336 where it determines whether the value for α is closer to the average β value than it is to the average α value. If the a value is closer to the average β value than it is to the average α value, the result of decision 336 is YES. In that event, in step 340, the statistical analyzer 224 discards the value for β and sets β equal to the value of α. If the value of α is not closer to the average β value than it is to the average α value, the result of decision 336 is NO. In that event, or upon completion of step 340, the statistical analyzer 224 repeats this process for each of the 12 (α, β) pairs.

Alternatively, the statistical analyzer 224 determines the confidence factor, which is a measure of the confidence in the calculation of α. As previously described, there are certain circumstances in which the calculated value for α is discarded and the value for β is used in its place (i.e., β is relabeled as α). To determine the confidence factor, the statistical analyzer 224 tracks the previous 12 α values and determines the average value, and the average deviation. If the calculated value for α is far from the average deviation of the previous 12 measurements, and the current value for β is approximately equal to the average value, the statistical analyzer 224 discards the value for α and uses the value for β in its place. The statistical analyzer 224 then determines the confidence value based on how many calculated values were discarded in the previous 12 measurements. If no α values were discarded in the previous 12 measurements, the confidence factor is 12/12=100%. However, if one α value was discarded in the previous 12 measurements, the confidence factor is 11/12=92%. In this manner, the system 200 provides a statistical measure of the confidence in the current measurement for α.

Another potential drawback to the measurement technique used by the system 200 is possible system instability. With reference to FIG. 10A, it is known that the first α curve 260 and the first β curve 264 asymptotically approach an intersection 270 between the first α curve and the first β curve. If there is any error in the value one parameter in the area of the intersection 270, the error is magnified for the second parameter. For example, consider two values for α, designated as $\alpha_1$ and $\alpha_2$, respectively, on the first β curve 264. Although the values for $\alpha_1$ and $\alpha_2$ differ by less than 0.1, this difference results in a potential error of more than 0.3 in the value of β. This type of error magnification can lead to potential system instability. However, the use of multiple windows avoids the system instability by assuring that accurate values are selected for α and β.

Following this process for each of the 12 (α, β) pairs, the statistical analyzer 224 recalculates the average values for α and β, as well as the mean deviation values for α and β in step 342. In step 344, the statistical analyzer 224 determines whether the deviation of α is less than 0.05. If the deviation of α is less than 0.05, the result of decision 344 is YES, and the system ends the process in step 352. If the deviation of α is not less than 0.05, the result of decision 344 is NO. In that event, the statistical analyzer 224 moves to decision 346 where it tests whether the deviation of β is less than 0.05 and the deviation of α is greater than 0.1. If the deviation of β is less than 0.05 and the deviation of α is greater than 0.1, the result of decision 346 is YES. In that event, in step 350, the statistical analyzer 224 sets the average value of α equal to the average value for β and ends the measurement process in step 352. If the result of decision 346 is NO, in step 348, the statistical analyzer 224 eliminates the farthest outlying values of α and β. Following step 348, the statistical analyzer 224 loops back to step 326 where it recalculates average values for α and β and mean deviation values for α and β. This process is repeated until the deviation of α is less than 0.05. Following this process, the value of α and β may be displayed. The calculated value for α is also used in a conventional manner to determine the $S_pO_2$. This process is continually repeated for each new determination of an (α, β) pair. Thus, the value for α is determined based on the statistical analysis of a plurality of previous (α, β) pairs.

Figure 13A:
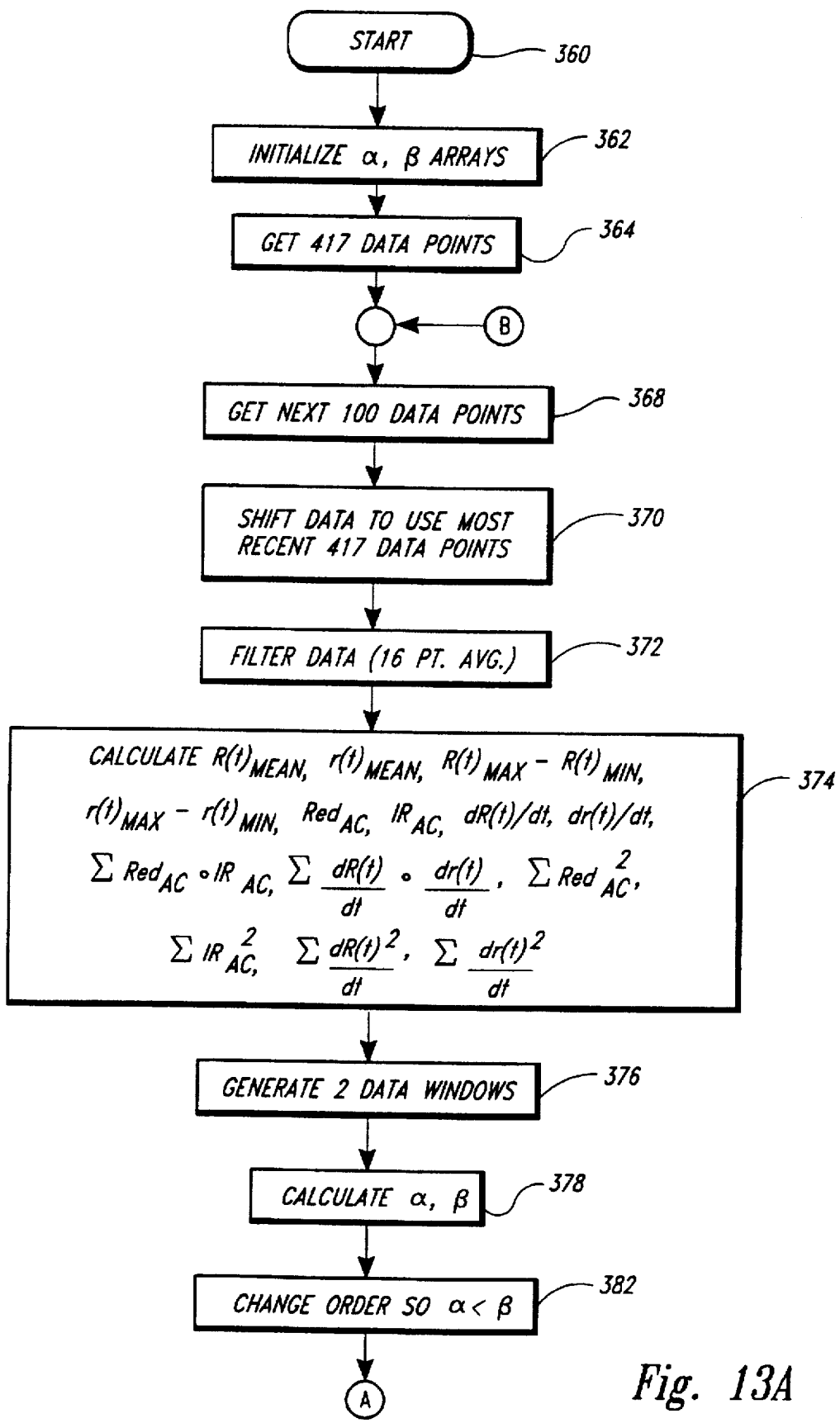
FIG. 13A and 13B are flow charts illustrating one embodiment of the measurement process by the system of FIG. 9.
Figure 13B:
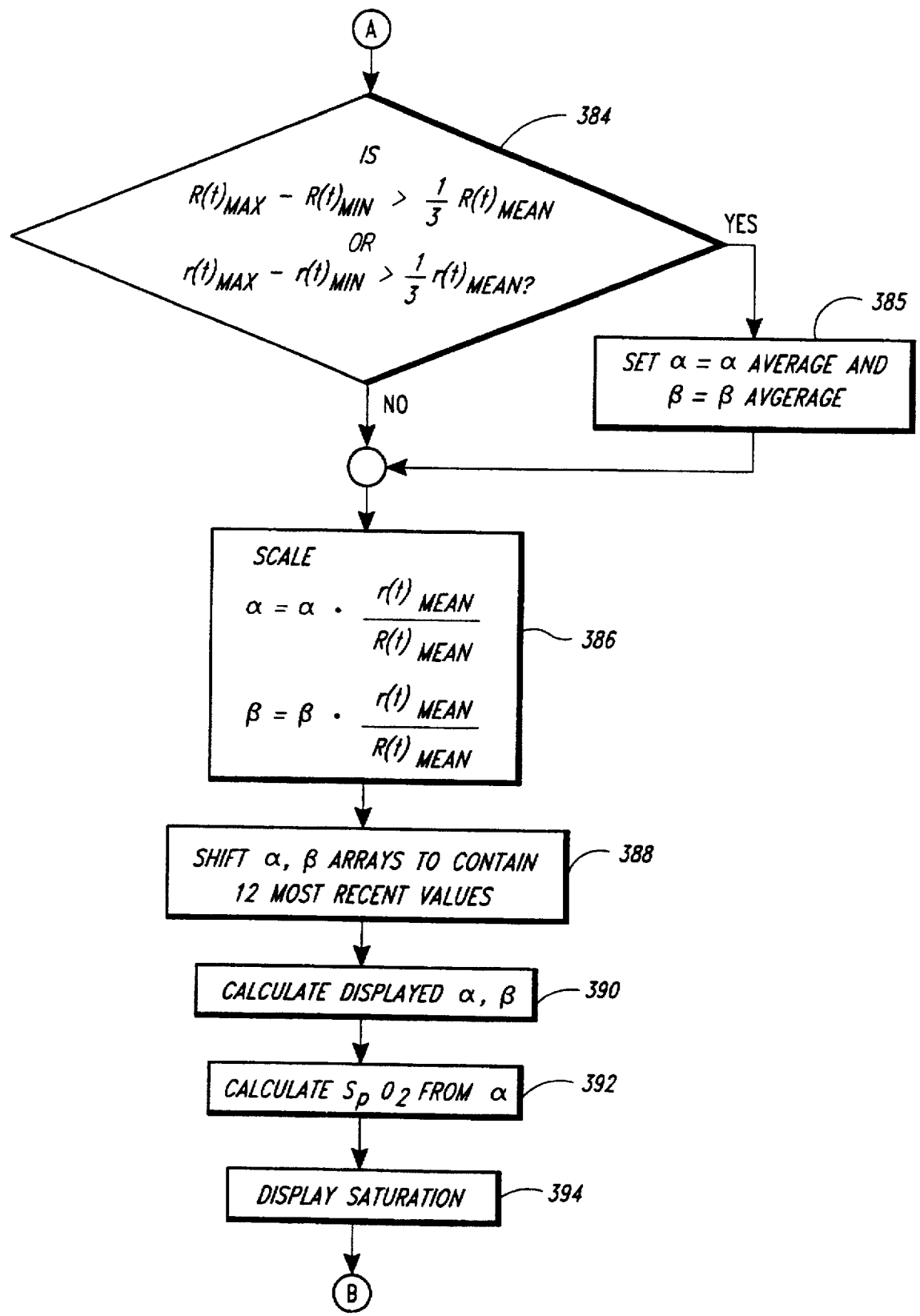

In one previously described embodiment of the system 200 the first and second data windows 302 and 304 (see FIG. 11B) were derived using the AC component of the digitized signals 184 and 186 for the first data window and the derivative of the digitized signals 184 and 186 for the second data window. The example above utilized Equation 21, which involves a number of integrals. However, as those skilled in the art will recognize, these calculations may be performed on the individual data points by summing various values. This is illustrated in the flow chart of FIGS. 13A and 13B. At the start 360, no data measurements have been made. The system 200 initializes the α and β arrays, which are stored in the α value storage area 218 (see FIG. 9) and the β value storage area 220, respectively. In step 364, the system 200 retrieves 417 data points from the first and second data storage areas 204 and 206, respectively. The system 200 then enters the measurement loop. In step 368, the system gets an additional 100 data points. It should be noted that measurements are always done on the most recent set of 417 data points. In step 370, the system 200 shifts the data to use the most recent 417 data points. In step 372, the system 200 filters the data in the first and second storage areas 204 and 206 using a 16 point average. This type of data averaging is well known to those skilled in the art and will not be described herein.

In step 374, the mathematical processor 210 (see FIG. 9) calculates a number of different values using the 417 data points in the first and second data storage areas 204 and 206. These calculations include the mean, AC component, and derivative of each of the digitized signals 184 and 186. In addition, the mathematical processor 210 calculates the sums of the square of the AC components, as previously described, the sum of squares of the derivative of the digitized signals 184 and 186, as well as the sums of the product of the AC components of the digitized signals and the sum of the product of the derivative of the digitized signals. The technique used to determine the mean value, the AC component, and the derivative has been previously described. In step 376, the window generator 214 generates the two data windows, as previously described. The first data window 302 (see FIG. 11B) is generated using the AC component of the digitized signals 184 and 186, while the second data window 304 is generated using the derivative of the digitized signals.

In step 378, the calculator 216 (see FIG. 9) calculates values for α and β using the following equation:

$$(\alpha,\beta) = \frac{(-b \pm (b^2 - 4ac)^{1/2})}{2a} \quad (23)$$

where $$a = \Sigma \frac{dr(t)^2}{dt} \cdot \Sigma Red_{AC} \cdot IR_{AC} - \Sigma IR_{AC}^2 \cdot \Sigma \frac{dR(t)}{dt} \cdot \frac{dr(t)}{dt},$$

$$b = \Sigma \frac{dR(t)^2}{dt} \cdot \Sigma IR_{AC}^2 - \Sigma \frac{dr(t)^2}{dt} \cdot \Sigma Red_{AC}^2, \text{ and}$$

$$c = \Sigma Red_{AC}^2 \cdot \Sigma \frac{dR(t)}{dt} \cdot \frac{dr(t)}{dt} - \Sigma \frac{dR(t)^2}{dt} \cdot \Sigma Red_{AC} \cdot IR_{AC}.$$

It should be noted that equation (23) is equivalent to equation (21) where the first data window 302 (see FIG. 11B) is the derivative of the digitized signals 184 and 186, while the second data window 304 is the AC component of the digitized signals.

As previously discussed, it is not initially known which of the values corresponds to α and which value corresponds to β. However, in step 382, the system changes the order such that α is less than β to correspond with Equation (22). In decision 384, the statistical analyzer 224 (see FIG. 9) determines whether the values for α and β are reasonable from a statistical point of view. Specifically, in decision 384, the statistical analyzer 224 determines whether the maximum value for the digitized signal 184 minus the minimum value for digitized signal is greater than one-third of the mean value for the digitized signal 184. In addition, the statistical analyzer 224 determines whether the maximum value for the digitized signal 186 minus the minimum value for that digitized signal is greater than one-third of the mean value for the digitized signal 186. If either of the maximum minus minimum values exceeds one-third of the mean value for the digitized signals 184 and 186, respectively, the result of decision 384 is YES, and the system 200 discards the current measurement in step 385, and uses the previous value for α in place of the current value.

If the result of decision 384 is NO, or upon completion of step 385, the system 200, in step 386, the statistical analyzer scales the value of α and β by multiplying the measured values by the mean values. As previously discussed, this effectively removes the DC component of the digitized signals 184 and 186. In step 388, the system 200 shifts the α and β arrays in the α value storage area 218 (see FIG. 9) and the β value storage area 220 to contain the 12 most recent values. In step 390, the system 200 uses the analysis described in FIGS. 12A and 12B to calculate displayed values for α and β. In step 392, the system calculates the oxygen saturation from the value of α in a conventional manner. In step 394, the system 200 displays the $S_pO_2$ value. Following the display of the $S_pO_2$ value in step 394, the system 200 returns to step 368 and retrieves the next 100 data points. In this embodiment, the system 200 performs a new measurement approximately once per second. This illustrates a technique used to determine the value for α using two data windows.

Alternatively, the system 200 can generate a plurality of windows and use other statistical techniques to derive a more accurate estimate for the value of α. A set of α values is generated for each of the plurality of data windows and the final α value is selected from this set. The statistical analyzer 224 applies conventional statistical analysis techniques to the plurality of windows to derive the final α value. For example, the system 200 can use the first, second and third data windows 306, 308, and 310 (see FIG. 11C) to generate three different (α, β) pairs.

Under ideal conditions, an intersection (not shown) of all three data windows 306, 308, and 310 on a graph would provide the correct values for α and β. However, under less than ideal conditions, it is unlikely that there will be a single intersection between the curves generated by the data windows 306, 308, and 310. The statistical analyzer 224 will determine the most accurate α value in a manner described below. If the principles of the system 200 are extended to a large number of data windows, a more accurate statistical analysis may be performed to determine the values of α and β. For example, if the data sample 300 (see FIG. 11A) is divided into 100 data windows (not shown) the system 200 would generate 100 (α, β) pairs.

The calculator 216 (see FIG. 9) uses equation (21) to solve for α and β in each of the 100 data windows. Thus, the calculator 216 determines 100 different values for the (α, β) pairs. The results of each of the calculations is stored in the α value storage area 218 as data bins. The use of bins is well known in the art and will only be described briefly herein.

Figure 14:
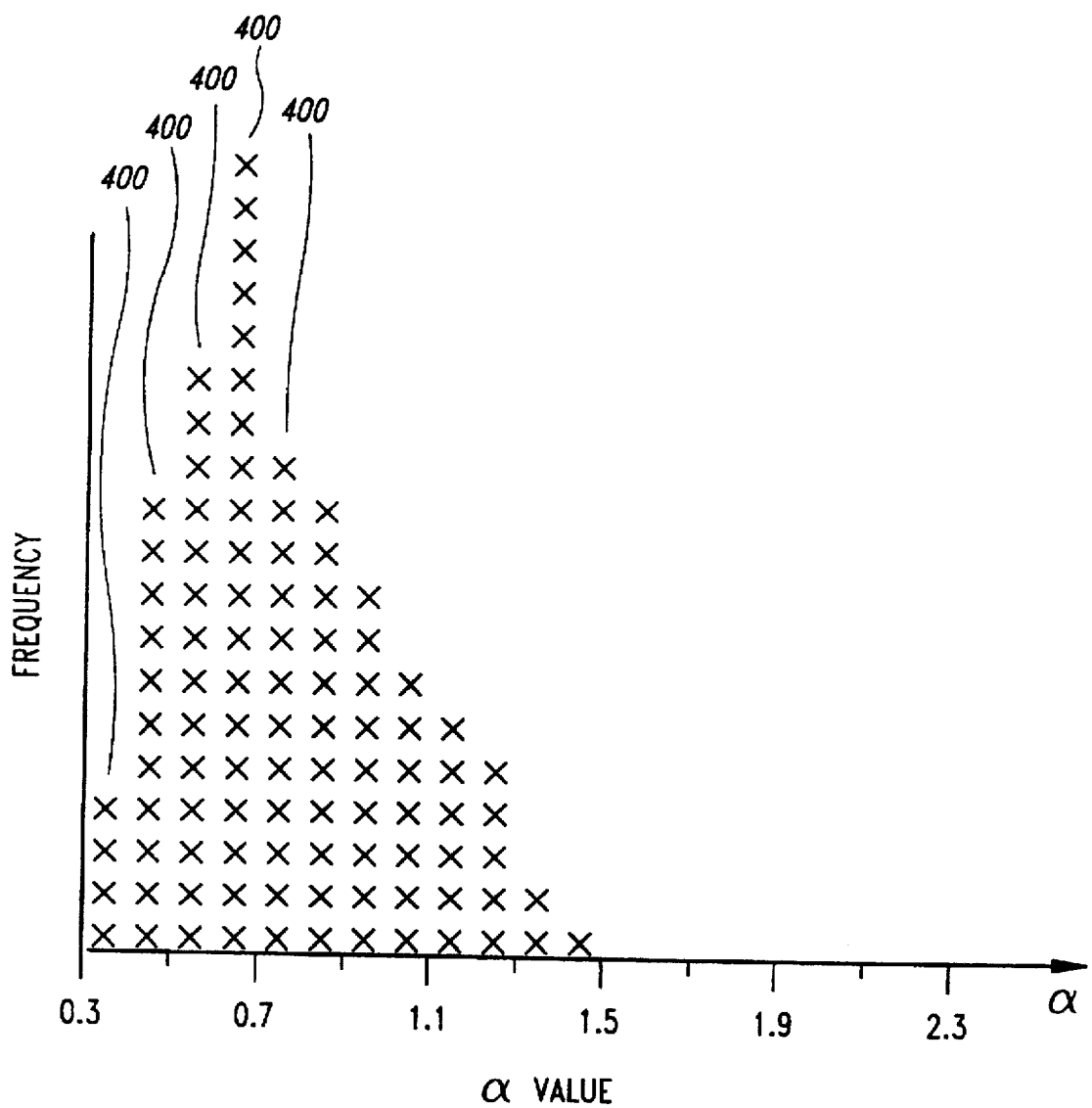
FIG. 14 illustrates the use of binned data used by the system of FIG. 9.
Figure 15:
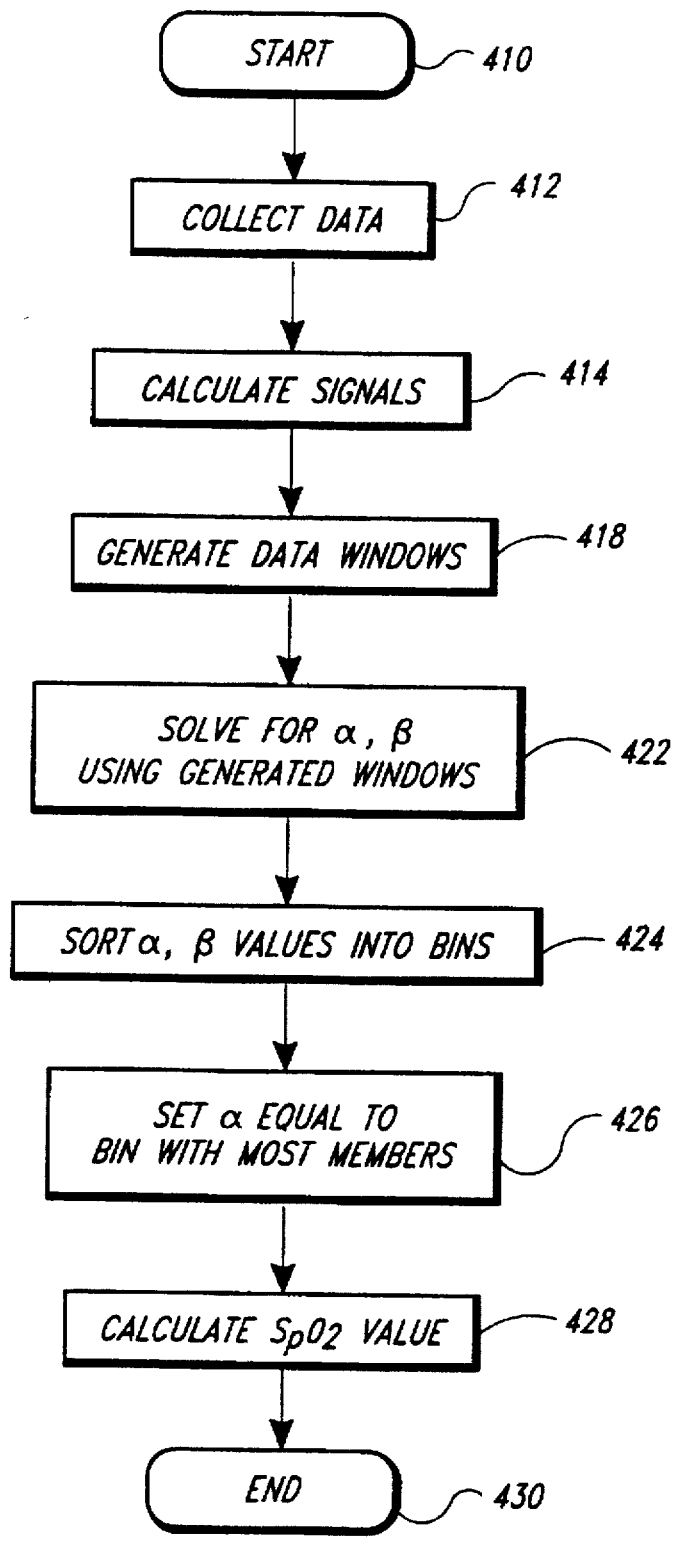
FIG. 15 is a flowchart of an alternative technique used by the system of FIG. 9.

The physiological range for α is subdivided into a number of ranges, designated as bins. Each time the calculator 216 determines a value for α, the corresponding bin is incremented. Thus, the α value storage area 218 contains a frequency distribution of α values. This is illustrated in FIG. 14 wherein the physiological range of values for α is subdivided into a plurality of bins 400. Each time the calculator 216 determines a value for α, the bin 400 corresponding to that value of α is incremented. This is indicated by an "X" in the bins 400. The bin 400 with the greatest number of occurrences can be selected as the best estimate for the value of α. Alternatively, the statistical analyzer 224 (see FIG. 9) can analyze the α bin data and determine the value for α based on the results of the statistical analysis. For example, the statistical analyzer 224 can calculate the standard deviation of the frequency distribution of data in the α value storage area 218 and select the value for α based on the standard deviation (S.D.). In one embodiment, the statistical analyzer 224 selects an average value for α based on ±1 S.D. Other forms of statistical analysis well known to those of ordinary skill in the art may also be used. The present invention is not limited by the specific type of statistical analysis performed on the data. It should also be noted that the bin width illustrated in FIG. 14 is provided as an example only. The bin width may be selected to provide the desired accuracy in determining the value for α. For example, the bin width illustrated in FIG. 13 is 0.1 However, if the physiological range for the value of α can be divided into bin widths of 0.01 to provide a more accurate estimate for α. The bin width and the nature of the statistical analysis can be altered to suit the particular application in addition, the bin width and statistical analysis can be altered depending on the computing power of the system 200.

The method used by the system 200 for multiple data window pairs is illustrated in the flow chart of FIG. 14. At the start 410, the sensor 2 (see FIG. 4) has been placed on the subject's finger tip. In step 412, data is collected from the subject in the manner previously described. It should be noted that the ADC 124 provides digitized samples for each of the measured signals, R(t) and r(t). The digitized signals 184 and 186 (see FIG. 9) are stored in the first data storage area 204 and the second data storage area 206, respectively. It should be noted, that while FIG. 11A illustrates a single data sample 300, the system 200 generates a data sample 300 for each of the digitized signals 184 and 186. In step 414, the mathematical processor 210 (see FIG. 9) calculates the derivatives, averages and the like, as described above. In step 418, the window generator 214 generates the eight pairs of data windows described above.

The calculator 216 solves for the α and β values in step 422 for all combinations of data windows or for selected combinations of data windows. In step 424 the α values and β values determined by the calculator 216 are stored in the α value storage area 218 and the β value storage area 220, respectively. In step 426, the system 200 sets α equal to the bin having the greatest number of occurrences. As discussed above, the statistical analyzer 224 may also perform statistical analyses on the data in the α value storage area 218. In step 428, the system 200 calculates the $S_pO_2$ value in a conventional manner using the look-up table 14 (see FIG. 4). The system 200 ends the measurement process at 430.

As discussed above, the calculator 216, in step 422, calculates the α and β values for each of the generated windows. However, as discussed above, a large number of data windows can be generated. For each member of a pair of windows, the calculator 216 can determined an (α, β) pair using either the AC components, the measured signals themselves, or the derivatives of the measured signals. The calculator 216 can calculate α and β values for each possible permutation of windows. For example, the calculator 216 can calculate an (α, β) pair using the derivative values in window 1 and the AC values in window 1, or the derivative values in window 1 with the AC values in window 2. Thus, for each of the eight pairs of windows, the calculator 216 can generate 6 (α, β) pairs (see Table 1), resulting in 48 different (α, β) pairs. The 48 (α, β) pairs will generally be different. The binning process described above is one technique used to select the proper value for α. However, those skilled in the art of statistical analysis, will readily recognize that other techniques may be used to determine the best estimate for the value of α. For example, sliding windows could be used instead of fixed bins. Alternatively, variable bin widths could be used. In yet another alternative, the system 200 subtracts the β count from the count for each of the bins 320 (see FIG. 12). Thus, the present invention is not limited by the specific form of the statistical analysis. Once the value of α has been determined, the $S_pO_2$ is determined in a conventional manner. In addition, the peak $S_pO_2$ value may be determined in a conventional manner using the $S_pO_2$ peak detector 136.

It should be noted that the principles of the present invention may be extended beyond the measurement of blood oxygen saturation. For example, a third light source (not shown) may be added to produce a third wavelength in the sensor 2 (see FIG. 4). Three ratios of light intensities (e.g., ratio of light source one to light source two, ratio of light source one to light source three, and ratio of light source two to light source three) can be derived from the light detector 10. The three ratios can be independently used to derive both the arterial oxygen saturation and the arterial carboxyhemoglobin saturation period. The present invention is also not limited solely to the use of optical sensors. Electrical sensors may derive physiological signals that can be processed according to the principles of the present invention. For example, electrical sensors can be used to derive a noise-free ECG signal. The electrical sensors each derive an ECG signal and the ratios of the ECG signals may be used to derive a noise-flee version of the true ECG signal.

In addition, the present invention may be used with a single sensor to measure a physiological parameter such as blood pressure. If the physiological parameter of interest is constant over the course of the measurement period, the data sample may be divided into a plurality of data windows and the principles of the present invention applied to pairs of data windows.

In operation, many of the components described above may be incorporated into a digital signal processor and/or a digital computer. The programming details of the digital signal processor and computer are well known to those of ordinary skill in the art and need not be discussed herein.

It is to be understood that even though various embodiments and advantages of the present invention have been set forth in the foregoing description, the above disclosure is illustrative only, and changes may be made in detail, yet remain within the broad principles of the invention. Therefore, the present invention is to be limited only by the appended claims.

What is claimed is:

1. A system for the enhancement of physiological signals for the measurement of blood oxygen in a subject, the system comprising:

first and second light sources to direct light toward the subject, said first and second light sources producing light of first and second wavelengths, respectively;

a light detector positioned to detect first and second light signals after interacting with the subject and to generate first and second signals indicative of an intensity of said first and second detected light signals, respectively, said first generated signal having a first portion arising from light transmitted from said first source and a second portion arising from a first interference light source, said second generated signal having a first portion arising from light transmitted from said second source and a second portion arising from a second interference light source;

a window generator to generate first and second data windows derived from data comprising said first and second generated signals;

a storage location containing a mathematical relationship of said first and second portions of said first and second generated signals and a ratio of said first portion of said first generated signal to said first portion of said second generated signal; and a calculator using said mathematical relationship to generate first and second functions using said first and second data windows, respectively, said first and second functions having a point of intersection indicative of said ratio.

2. The system of claim 1 wherein said ratio is indicative of blood oxygen saturation in the subject, the system further including a look-up table containing data relating said ratio to said blood oxygen saturation.

3. The system of claim 1 wherein said first data window is a derivative of said first and second generated signals.

4. The system of claim 1 wherein said first data window is an alternating current (AC) component of said first and second generated signals.

5. The system of claim 1 wherein said first data window is derived from a group of signals comprising said first generated signal, a mathematical derivative of said first generated signal, said second generated signal, a mathematical derivative of said second generated signal, a combination of said first and second generated signals, and a mathematical derivative of said combination of said first and second generated signals.

6. The system of claim 5 wherein said window generator calculates an average value for each of said group of signals and data having a data value less than said average for a particular one of said group of signals is placed in said first data window and data having said data value greater than or equal to said average for said particular one of said group of signals is placed in said second data window.

7. The system of claim 5 wherein said window generator calculates an average value for each of said group of signals and data having a data value less than said average for a first one of said group of signals is placed in said first data window and data having said data value greater than or equal to said average for a second one of said group of signals is placed in said second data window.

8. The system of claim 1 wherein said mathematical relationship has the following form:

$$\alpha i = Fi(\beta) = \frac{\int_t R_i^2(t) - \beta \int_t R_i(t)r_i(t)}{\int_t R_i(t)r_i(t) - \beta \int_t r_i^2(t)}$$

where $\alpha$ is said ratio, $i=1$ to 2 for said first and second data windows, respectively, $R_i(t)$ is said first generated signal in the ith data window, $r_i(t)$ is said second generated signal in the ith data window, and $\beta$ represents a ratio variable of a portion of said first generated signal to a corresponding portion of said second generated signal.

9. The system of claim 8 wherein said calculator is configured to solve for a pair of values for $\alpha$ and $\beta$, respectively, by setting $F_1(\beta)=F_2(\beta)$ and solving for the ($\alpha$, $\beta$) pair using a mathematical function having the following form:

$$(\alpha,\beta) = \left\{ \begin{array}{c} \int_t r_1^2(t) \int_t R_2^2(t) - \int_t R_1^2(t) \int_t r_2^2(t) \\ \mp \left[ \begin{array}{c} \left( \int_t r_1^2(t) \int_t R_2^2(t) - \int_t r_1^2(t) \int_t R_2^2(t) \right)^2 - \\ 4 \times \left( \int_t r_1^2(t) \int_t R_2(t)r_2(t) - \int_t R_1(t)r_1(t) \int_t r_2^2(t) \right) \times \\ \left( \int_t R_1(t)r_1(t) \int_t R_2^2(t) - \int_t R_1^2(t) \int_t R_2(t)r_2(t) \right) \end{array} \right]^{1/2} \\ \left[ 2 \times \left( \int_t r_1^2(t) \int_t R_2(t)r_2(t) - \int_t R_1(t)r_1(t) \int_1 r_2^2(t) \right) \right]^{-1} \end{array} \right\} \times$$

10. The system of claim 1 wherein the physiological signals are also indicative of blood carbon monoxide levels, the system further comprising a third light source generating a third wavelength of light different from said first and second wavelengths, said detector being positioned to detect a third light signal from said third light source after interacting with the subject and to generate a third signal indicate of an intensity of said third detected light signal, said third generated signal having a first portion arising from light transmitted from said third source and a second portion arising from a third interference light source, said window generator generating a third data window derived from said third generated signal, said first and second functions having a point of intersection indicative of said first ratio related to blood oxygen saturation, said calculator also using said mathematical relationship to generate a third function using said second and third data windows, respectively, said second and third functions having a point of intersection indicative of said second ratio related to blood carboxyhemoglobin saturation.

11. A method using a computer for the enhancement of physiological signals for the measurement of blood oxygen in a subject, the method comprising the steps of:

directing first and second light sources toward the subject, said first and second light sources producing light of first and second wavelengths, respectively;

detecting first and second light signals after interaction with the subject and generating signals indicative of an intensity of said first and second detected light signals, said first generated signal having a first portion arising from light transmitted from said first source and a second portion arising from a first interference light source, said second generated signal having a first portion arising from light transmitted from said second source and a second portion arising from a second interference light source;

generating a plurality of data windows derived from data comprising said first and second generated signals; and using a mathematical relationship of said first and second portions of said first and second generated signals and a ratio of said first portion of said first generated signal to said first portion of said second generated signal to generate a plurality of functions from said plurality of data windows, respectively, said plurality of functions having a solution value indicative of said ratio.

12. The method of claim 11 wherein said plurality of functions comprises first and second functions, said first and second functions having an intersection indicative of said ratio.

13. The method of claim 11 wherein said plurality of functions comprises first, second, and third functions, said ratio being statistically derived based on said solution values for said first, second, and third functions.

14. The method of claim 11 wherein said ratio is indicative of blood oxygen saturation in the subject, the method further including the step of using a look-up table containing data relating said ratio to said blood oxygen saturation to determine the blood oxygen level in the subject.

15. The method of claim 11 wherein a first of said plurality of data windows is a derivative of said first generated signal.

16. The method of claim 11 wherein a first of said plurality of data windows is an alternating current (AC) component of said first generated signal.

17. The method of claim 11 wherein a first of said plurality of data windows is derived from a group of signals comprising said first generated signal, a mathematical derivative of said first generated signal, said second generated signal, a mathematical derivative of said second generated signal, a combination of said first and second generated signals, and a mathematical derivative of said combination of said first and second generated signals.

18. The method of claim 11, further including the steps of calculating an average value for each of said group of signals and placing data whose value is less than said average for a particular one of said group of signals in a first of said plurality of data windows and placing data whose value is greater than or equal to said average for said particular one of said group of signals in a second of said plurality of data windows.

19. The method of claim 11, further including the steps of calculating an average value for each of said group of signals and placing data whose value is less than said average for a particular one of said group of signals in a first of said plurality of data windows and placing data whose value is greater than or equal to said average for a second one of said group of signals in a second of said plurality of data windows.

20. The method of claim 11 wherein the physiological signals are also indicative of blood carbon monoxide levels and said step of directing light sources includes directing first, second, and third light sources toward the subject and said step of detecting includes detecting first, second, and third light signals after interaction with the subject and generating first, second and third signals indicative of an intensity of said first, second and third detected light signals, respectively, said third generated signal having first portion arising from light transmitted from said third light source and a second portion arising from a third interference light source, said step of generating data windows generating first, second, and third data windows derived from said first, second and third generated signals, respectively, said step of generating said plurality of functions using said mathematical relationship to generate a second ratio of said first portion of a first of said plurality of generated signals to said first portion of a third of said plurality of said generated signals, and using said mathematical relationship to generate first and second functions using said first and second data windows, respectively, said first and second functions having a point of intersection indicative of said first ratio related to blood oxygen saturation and using said mathematical relationship to generate a third function using said second and third data windows, respectively, said second and third functions having a point of intersection indicative of said second ratio related to blood carboxyhemoglobin saturation.

21. A system for the enhancement of physiological signals for the measurement of blood oxygen in a subject, the system comprising:

first and second light sources to direct light toward the subject, said first and second light sources producing light of first and second wavelengths, respectively;

a light detector positioned to detect first and second light signals after interaction with the subject and to generate first and second signals indicative of an intensity of said first and second detected light signals, respectively, said first generated signal having a first portion arising from light transmitted from said first source and a second portion arising from a first interference light source, said second generated signal having a first portion arising from light transmitted from said second source and a second portion arising from a second interference light source;

a window generator to generate a plurality of data windows derived from data comprising said first and second generated signals;

a storage location containing a mathematical relationship of said first and second portions of said first and second generated signals and a ratio of said first portion of said first generated signal to said first portion of said second generated signal; and a calculator using said mathematical relationship to generate a plurality of functions from said plurality of data windows, respectively, said plurality of functions having a final solution value indicative of said ratio.

22. The system of claim 21 wherein said ratio is indicative of blood oxygen saturation in the subject, the system further including a look-up table containing data relating said ratio to said blood oxygen saturation.

23. The system of claim 21 wherein a first of said plurality of data windows is derived from a group of signals comprising said first generated signal, a mathematical derivative of said first generated signal, said second generated signal, a mathematical derivative of said second generated signal, a combination of said first and second generated signals, and a mathematical derivative of said combination of said first and second generated signals.

24. The system of claim 23 wherein said window generator calculates an average value for each of said group of signals and data having a data value less than said average for a particular one of said group of signals is placed in said first data window and data having said data value greater than or equal to said average for said particular one of said group of signals is placed in a second of said plurality of data windows.

25. The system of claim 23 wherein said window generator calculates an average value for each of said group of signals and data having a data value less than said average for a first one of said group of signals is placed in said first data window and data having said data value greater than or equal to said average for a second one of said group of signals is placed in a second of said plurality of data windows.

26. The system of claim 21 wherein each plurality of functions results in a solution value, said calculator determining said final solution value based on said solution values for said plurality of functions.

27. The system of claim 26 wherein said calculator includes a statistical analyzer to evaluate said solution values for said plurality of functions and determine said final solution value based on statistical analysis of said solution values for said plurality of functions.

28. The system of claim 21 wherein the physiological signals are indicative of blood carbon monoxide levels, the system further comprising a third light source generating a third wavelength of light different from said first and second wavelengths, said detector being positioned to detect a third light signal from said third light source after interaction with the subject and to generate a third signal indicative of an intensity of said third detected signal, said third generated signal having a first portion arising from light transmitted from said third source and a second portion arising from a third interference light source, said window generator generating first, second, and third data windows derived from said first, second and third generated signals, said mathematical relationship also including a first ratio of said first portion of said first generated signal to said first portion of said second generated signal and a second ratio of said first portion of said first generated signal to said first portion of said third generated signal, said calculator using said mathematical relationship to generate first and second functions using said first and second data windows, respectively, said first and second functions having a solution value indicative of said first ratio related to blood oxygen saturation, said calculator using said mathematical relationship to generate a third function using said first and third data windows, respectively, said second and third functions having a solution value indicative of said second ratio related to blood carboxyhemoglobin saturation.

* * * * *

Adverse Decisions in Interference

Patent No. 5,687,722, Jonathan Tien, and David R. Marble, SYSTEM AND METHOD FOR THE ALGEBRAIC DERIVATION OF PHYSIOLOGICAL SIGNALS, Interference No. 105,478, final judgment adverse to the patentees rendered, November 24, 2006, as to claims 1-28.
*(Official Gazette March 20, 2007)*